United States Patent
Kimizuka

(10) Patent No.: US 7,641,861 B2
(45) Date of Patent: Jan. 5, 2010

(54) MICROFLUIDIC DEVICE HAVING MICROCHIPS

(75) Inventor: Genichi Kimizuka, Saitama (JP)

(73) Assignee: Enplas Corporation, Saitama (JP)

( * ) Notice: Subject to any disclaimer, the term of this patent is extended or adjusted under 35 U.S.C. 154(b) by 138 days.

(21) Appl. No.: 11/861,517

(22) Filed: Sep. 26, 2007

(65) Prior Publication Data

US 2008/0260591 A1    Oct. 23, 2008

Related U.S. Application Data

(62) Division of application No. 10/832,848, filed on Apr. 27, 2004, now Pat. No. 7,422,725.

(30) Foreign Application Priority Data

May 1, 2003  (JP) .............................. 2003-126198
Nov. 18, 2003  (JP) .............................. 2003-388014

(51) Int. Cl.
*B01L 3/02* (2006.01)
(52) U.S. Cl. ..................................................... 422/100
(58) Field of Classification Search .................. 422/100
See application file for complete search history.

(56) References Cited

U.S. PATENT DOCUMENTS 4,417,732 A * 11/1983 Guill .......................... 273/238

(Continued)

FOREIGN PATENT DOCUMENTS

WO    WO 0053279 A1 *  9/2000

OTHER PUBLICATIONS

Lin, Y.; Matson, D. W.; Kurath, D. E.; Wen, J. Y.; Xiang, F.; Bennett, W. D.; Martin, P. M.; Smith, R. D. "Microfluidic Devices on Polymer Substrates for Bioanalytical Applications." Conference: 3rd International Conference on Microreaction Technology; Microreaction Technology: Industrial Prospects IMRET Apr. 3, 1999.*

*Primary Examiner*—Walter D Griffin
*Assistant Examiner*—Bobby Ramdhanie
(74) *Attorney, Agent, or Firm*—Bachman & LaPointe, P.C.

(57) ABSTRACT

After a second plate member 3 is inserted into a space which is surrounded by side walls 6a through 6d of a first plate member 2, the bonded surface 3a of the second plate member 3 is bonded and fixed to the bonded surface 2a of the first plate member 2 by an adhesive to form a sample handling unit 1. At this time, the second plate member 3 is positioned by protrusions 35 and 36 of the first plate member 2 in X and Y directions, and positioned and fixed by holding members 8 through 13 and inside holding members 26 and 27 in Z directions (normal directions on an external surface 7). A microfluidic device 101 includes microchips 106 through 108 of plural kinds having passages 132 through 134 for transporting a sample, and a base member 102 on which the microchips 106 through 108 are arranged. After the base member 102 and the microchips 106 through 108 are separately formed, microchips 106 through 108 of kinds necessary for intended purpose, such as analysis of the sample, are selected to be suitably combined to be positioned and fixed on the base member 102 to form the microfluidic device 101. By causing the positioning holes 127 of the microchips 106 through 108 to engage the positioning protrusions 128 of the base member 102, the microchips 106 through 108 are positioned with respect to the base member 102.

7 Claims, 18 Drawing Sheets

U.S. PATENT DOCUMENTS

| | | | |
|---|---|---|---|
| 5,090,701 A * | 2/1992 | Chang | 273/157 R |
| 5,356,151 A * | 10/1994 | Abecassis | 273/243 |
| 5,764,518 A * | 6/1998 | Collins | 700/95 |
| 6,267,858 B1 * | 7/2001 | Parce et al. | 204/600 |
| 6,488,895 B1 * | 12/2002 | Kennedy | 422/100 |
| 6,827,095 B2 * | 12/2004 | O'Connor et al. | 137/15.01 |
| 2004/0087033 A1 * | 5/2004 | Schembri | 436/180 |

* cited by examiner

MICROFLUIDIC DEVICE HAVING MICROCHIPS

CROSS REFERENCE TO RELATED APPLICATIONS

This application is a divisional application of U.S. Ser. No. 10/832,848 filed Apr. 27, 2004, now U.S. Pat. No. 7,422,725.

BACKGROUND OF THE INVENTION

1. Field of the Invention

The present invention generally relates to a sample handling unit applicable to a microchip, and a microfluidic device having a plurality of microchips. More specifically, the invention relates to a sample handling unit capable of being widely applied to a microchip (e.g., a microchip of a type for moving a very small amount of sample (specimen) in a microchannel, or a microchip of a type for housing and holding a very small amount of sample (specimen) in a microwell) or the like in a technical field called integrated chemistry, and the invention also relates to a microfluidic device which is used for carrying out the separation, analysis or the like of a very small amount of sample in a fluid, or for carrying out the mixing, reaction, concentration or the like of a very small amount of sample.

2. Description of the Prior Art

In recent years, there is known a technique called integrated chemistry for forming a fine groove (recessed portion) having a width and depth of about tens to two hundreds micrometers in a microchip (sample handling unit) of a glass or plastic, to use the fine groove as a liquid passage, reaction vessel or separation/purification detecting vessel, to integrate a complicated chemical system into the microchip. According to such integrated chemistry, a microchip (Lab-on-a-chip) having a fine groove used in various tests is called μ-TAS (Total Analytical System) if the use of the microchip is limited to analytical chemistry, and the microchip is called microreactor if the use of the microchip is limited to a reaction. When various tests, such as analyses, are carried out, integrated chemistry has advantages that the time to transport diffuse molecules is short due to small space and that the heat capacity of a liquid phase is very small. Therefore, integrated chemistry is noticed in the technical field wherein a micro space is intended to be utilized for carrying out analysis and chemical synthesis. Furthermore, the term "test" means to carry out any one or combination of operations and means, such as analysis, measurement, synthesis, decomposition, mixing, molecular transportation, solvent extraction, solid phase extraction, phase separation, phase combination, molecule acquisition, culture, heating and cooling.

In such integrated chemistry, a capillary electrophoresis chip used in a test in the field of, e.g., biochemistry, is a chip of a glass or plastic which has a fine groove or circular recessed portion having a width and depth of about 10 to 200 micrometers to use the fine groove or recessed portion as a liquid passage or reaction vessel to separate and identify a very small amount of vital material, such as a nucleic acid or protein, or another low molecular material, so that the material to be treated therein has a very small volume of nanoliters to picoliters. Therefore, it is required to precisely form the fine groove.

As methods for forming a fine groove (a hollow portion) in a glass or plastic, there are blow molding and lost-core methods. By these methods, it is difficult to precisely form a fine groove having a cross section tens micrometers square. Therefore, there is often adopted a method for forming a fine groove in a surface of a first plate member (a first member) of a glass, plastic or silicon to bond a second plate member (a second member), which is formed of the same material as that of the first plate member so as to have the same size as that of the first plate member, to the surface of the first plate member having the fine groove by adhesion or welding to form a microchip as a sample handling unit (see Japanese Patent Laid-Open Nos. 2000-246092 and 2000-288381).

However, if the sample handing device, which is formed by bonding the first plate member to the second plate member by adhesion or welding, slides down and drops from an experimenter's hand onto the floor or the like when various tests are carried out, the shock of the collision with the floor or the like causes external force, such as shearing force, to act on the bonded surface of the first plate member to the second plate member, so that there is the possibility that the bonded surface may be partially broken (cracked) to damage sealing performance around a microchannel to damage the function of the microchannel and/or to peel the first plate member off from the second plate member.

In recent years, there have been prosperously studied devices capable of carrying out separation, analysis, mixing, reaction, concentration or the like of a sample in a fine space called Lab-on-a-chip, μ-TAS, microreactor or the like. In such devices, there are many advantages in that the amount of a sample to be analyzed can be decreased, the size of system can be decreased, the time to carry out analysis or the like can be shortened, and so forth.

For example, there are known microfluidic devices for electrophoresis wherein a fine passage (microchannel) is formed in a fine space for separating and analyzing vital molecules, such as DNA and proteins, which serve as samples (specimens) and microfluidic devices for POC (Point-of-Care) wherein a reservoir or fine passage is formed for mixing a collected blood with a plurality of predetermined solutions to observe a catalytic reaction. Usually, these microfluidic devices have a single microfluidic system.

On the other hand, there are known microfluidic devices having a plurality of microfluidic systems (see WO99/15876, WO99/15888, and US 2003/0006141A1).

However, in these conventional devices, a large number of microchannels comprising fine grooves must be formed in a chip so as to be set in array. If such a chip having a large number of microchannels is intended to be formed by injection molding, it is difficult to work a die. Therefore, the cost of producing the die is very high, and the price of the chip is very high. Even if such a chip is formed by a working method other than injection molding, e.g., a working method utilizing a semiconductor working technique, such as photolithography, when a large number of microchannels comprising fine grooves are simultaneously formed in a chip (plate), the yields deteriorate to inhibit the price of the chip from decreasing.

In addition, in the above described conventional devices, a large number of microchannels are formed directly in a chip. Therefore, it is not possible to change the structure of the chip in accordance with intended purpose or the like, so that there is a problem in that the expensive chip can be only used for a specific intended purpose.

SUMMARY OF THE INVENTION

It is therefore an object of the present invention to eliminate the aforementioned problems and to provide a sample handling unit which is formed by bonding a plurality of members and which is capable of effectively preventing a bonded surface from being partially broken and preventing bonded members from being peeled off from each other even if shocks are given to the unit.

It is another object of the present invention to eliminate the aforementioned problems and to provide a microfluidic device capable of changing the structure of a chip in accordance with intended purpose or the like.

In order to accomplish the aforementioned and other objects, according to one aspect of the present invention, there is provided a sample handling unit for handling a sample, the unit comprising: a first member having a surface; and a second member having a surface which is bonded to the surface of the first member to define a space between the first and second members for handling a sample, the second member having a side face which extends from an edge of the surface of the second member, wherein the first member has a protruding wall which protrudes from the surface of the first member so as to face the side face of the second member.

Furthermore, throughout the specification, the term "sample" means a material used in various operations and means, such as such as analysis, measurement, synthesis, decomposition, mixing, molecular transportation, solvent extraction, solid phase extraction, phase separation, phase combination, molecule acquisition, culture, heating and cooling. For example, in an operation, such as analysis or measurement, the term "sample" means a specimen to be operated, and in a synthesis operation, the term "sample" means a raw material before synthesis or a compound or the like after synthesis.

In the above described sample handling unit, the space may be a space for allowing the sample to move therein, or a space for housing therein the sample. In addition, a second space may be defined between the first and second members, the space being a space for allowing the sample to move therein, and the second space being a space for housing therein the sample. The protruding wall is preferably positioned so as to face a corner of the second member. The protruding wall preferably protrudes from a plane including an opposite surface of the second member which is opposite to the surface of the second member. The protruding wall may have a protrusion which contacts the side face of the second member for positioning the second member with respect to the first member. The first member may have a holding member for biasing the second member toward the first member to hold the second member on the first member, or a pair of holding members for biasing the second member toward the first member to hold the second member on the first member. The holding member may have an engaging portion for engaging an opposite surface of the second member which is opposite to the surface of the second member. The second member may have an inclined surface in a portion facing the holding member, the inclined surface being inclined with respect to the surface of the second member, and the holding member may have an engaging portion for engaging the inclined surface of the second member to bias the second member toward the first member. One of the first and second members may have a hole, and the other of the first and second members may have a pair of inside holding members for engaging the hole to hold the second member on the first member. In this case, one of the pair of inside holding members may engage a first portion of the hole so as to bias the one of the first and second members in a first direction, and the other of the pair of inside holding members may engage a second portion of the hole, which is opposite to the first portion thereof, so as to bias the one of the first and second members in a second direction opposite to the first direction, the pair of inside holding members being associated with each other for holding the second member on the first member. In addition, the hole may have an engaged portion which protrudes toward the pair of inside holding members, and each of the pair of inside holding members may have an engaging portion which protrudes toward the hole, the engaging portion of each of the pair of inside holding members engaging the engaged portion of the hole so as to press the second member on the first member. The hole and the inside holding members may be arranged in the vicinity of the space defined between the first and second members. The inside holding members may be formed so as not to protrude from a plane including an opposite surface of the one of the first and second members, the opposite surface being opposite to the surface of the one of the first and second members. The holding member may have a protrusion which contacts the side face of the second member for positioning the second member with respect to the first member.

According to another aspect of the present invention, there is provided a sample handling unit for handling a sample, the unit comprising: a first member having a surface; and a second member having a surface which is bonded to the surface of the first member to define a space between the first and second members for handling a sample therein, the second member having a side face which extends from an edge of the surface of the second member, wherein the surface of the first member is larger than the surface of the second member so that the first member protrudes from the edge of the surface of the second member.

In this sample handling unit, the space may be a space for allowing the sample to move therein, or a space for housing therein the sample. In addition, a second space may be defined between the first and second members, the space being a space for allowing the sample to move therein, and the second space being a space for housing therein the sample. One of the first and second members may have a hole, and the other of the first and second members may have a pair of inside holding members for engaging the hole to hold the second member on the first member. In this case, one of the pair of inside holding members may engage a first portion of the hole so as to bias the one of the first and second members in a first direction, and the other of the pair of inside holding members may engage a second portion of the hole, which is opposite to the first portion thereof, so as to bias the one of the first and second members in a second direction opposite to the first direction, the pair of inside holding members being associated with each other for holding the second member on the first member. In addition, the hole may have an engaged portion which protrudes toward the pair of inside holding members, and each of the pair of inside holding members may have an engaging portion which protrudes toward the hole, the engaging portion of each of the pair of inside holding members engaging the engaged portion of the hole so as to press the second member on the first member.

According to a further aspect of the present invention, a microfluidic device comprises: a base member; and a plurality of microchips, each of which has a space defined therein for transporting a sample, the plurality of microchips being mounted on the base member so as to be set in array.

In this microfluidic device, each of the plurality of microchips may have a recessed portion which is closed by the base member to define the space. The plurality of microchips may be detachably mounted on the base member. The base member may have a chip pressing claw, and the plurality of microchips may be detachably held by the chip pressing claw of the base member. The space may be a passage for allowing the sample to move therein. The passage may have a storage portion for storing therein the sample. The storage portion of one of the plurality of microchips may be communicated with the storage portion of another of the plurality of microchips via a communication passage formed in the base member. One of adjacent two of the plurality of microchips may have an engaging protrusion which protrudes toward the other of the adjacent two of the plurality of microchips, and the other of the adjacent two of the plurality of microchips may have an engaged recess which is engaged with the engaging protrusion of the one of adjacent two of the plurality of microchips. The plurality of microchips may be positioned with respect to the base member by positioning means.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings:

FIG. 18A through 18C are plan views of microchips in the first preferred embodiment of the present invention, wherein FIG. 18A shows a microchip of the first kind, FIG. 18B shows a microchip of the second kind, and FIG. 18C shows a microchip of the third kind;

DESCRIPTION OF THE PREFERRED EMBODIMENTS

Referring now to the accompanying drawings, particularly to FIGS. 1 through 16, the preferred embodiments of a sample handling unit according to the present invention will be described below in detail. In each of the following preferred embodiments, a sample handling unit of a plastic used as a capillary electrophoresis chip will be described as an example.

Figure 1:
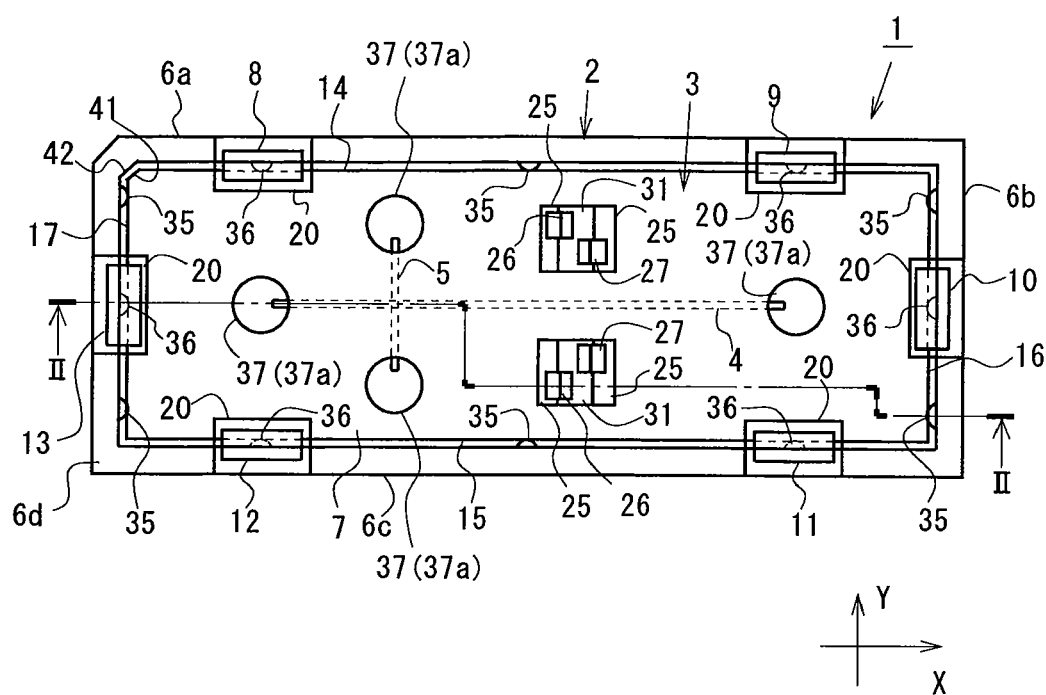
FIG. 1 is a plan view of a preferred embodiment of a sample handing unit according to the present invention.
Figure 2:
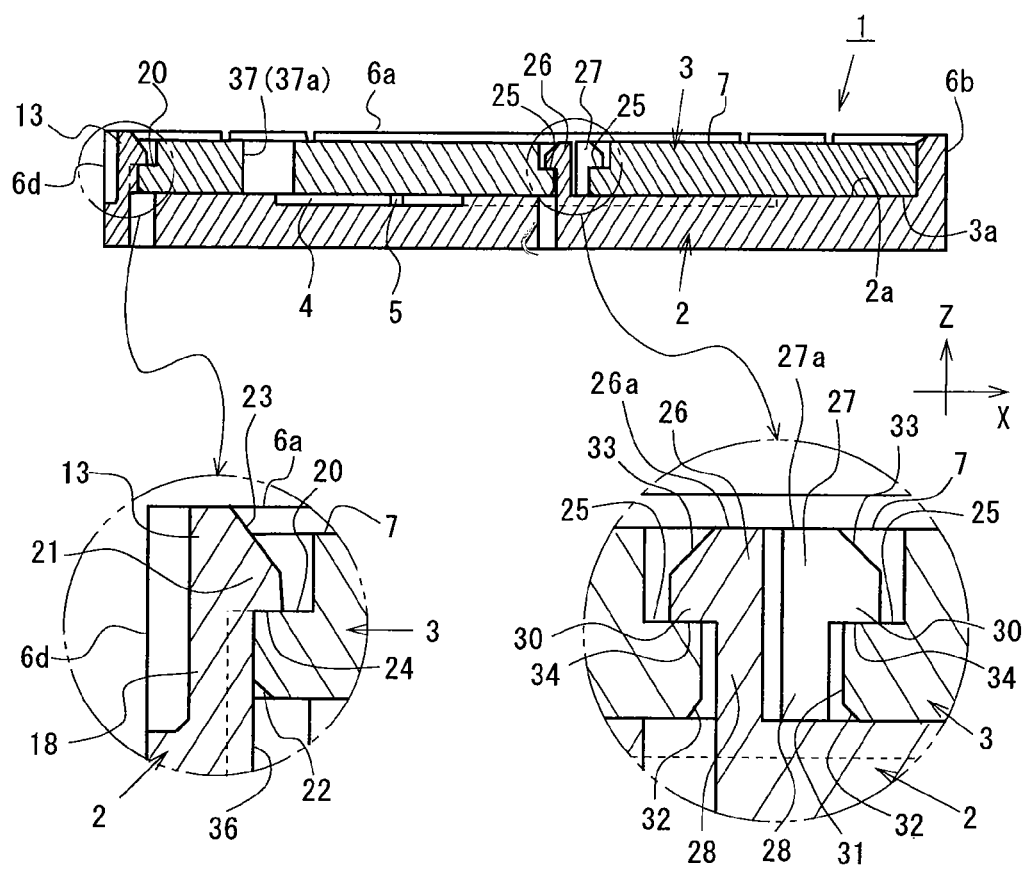
FIG. 2 is a sectional view of the sample handling unit taken along line II-II of FIG. 1.
Figure 3:
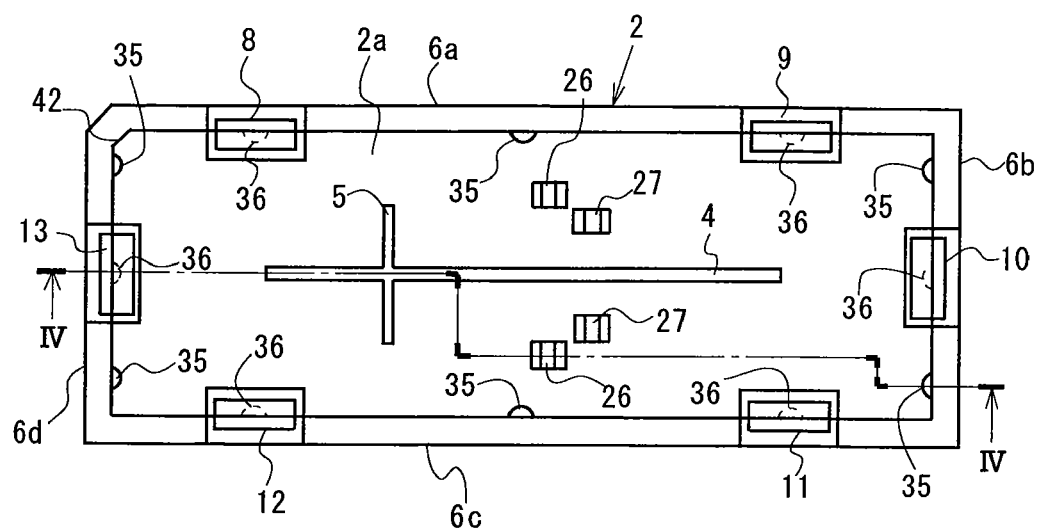
FIG. 3 is a plan view of a first plate member forming the sample handling unit of FIG. 1.
Figure 4:
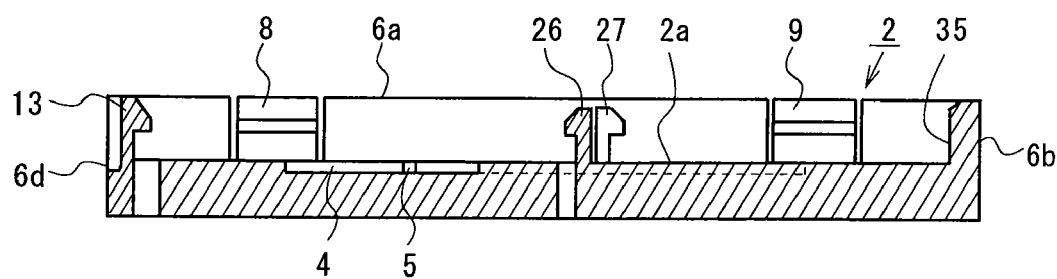
FIG. 4 is a sectional view of the first plate member taken along line IV-IV of FIG. 3.
Figure 5:
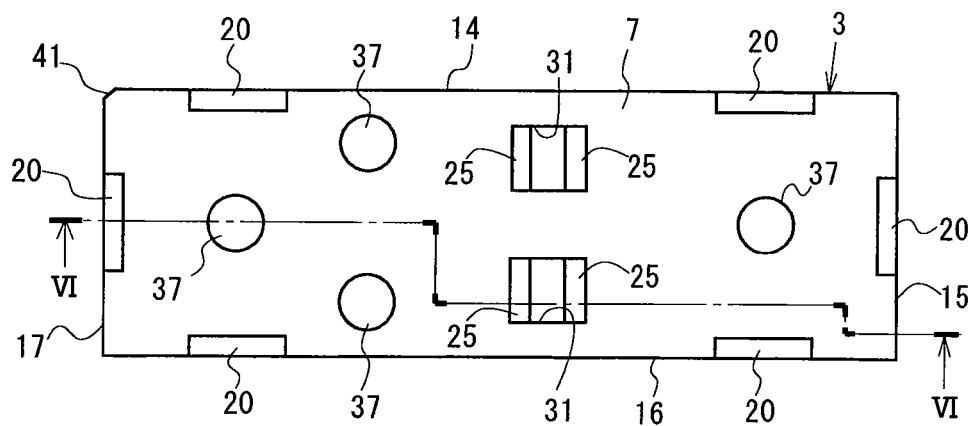
FIG. 5 is a plan view of a second plate member forming the sample handling unit of FIG. 1.
Figure 6:
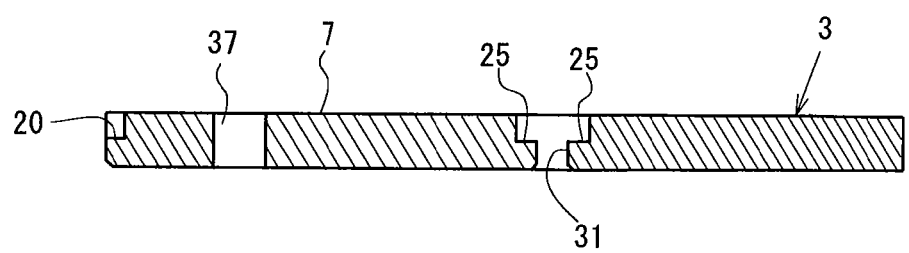
FIG. 6 is a sectional view of the second plate member taken along line VI-VI of FIG. 5.

FIGS. 1 through 6 show a preferred embodiment of a sample handling unit 1 according to the present invention. FIG. 1 is a plan view of the sample handling unit 1, and FIG. 2 is a sectional view of the sample handling unit 1 taken along line II-II of FIG. 1. FIG. 3 is a plan view of a first plate member (first member) 2 forming the sample handling unit 1 of FIG. 1, and FIG. 4 is a sectional view of the first plate member 2 taken along line IV-IV of FIG. 3. FIG. 5 is a plan view of a second plate member (second member) 3 forming the sample handling unit 1 of FIG. 1, and FIG. 6 is a sectional view of the second plate member 3 taken along line VI-VI of FIG. 5.

The sample handling unit 1 shown in these figures comprises the first plate member 2 and the second plate member 3 bonded and fixed thereto. The first and second plate members 2 and 3 forming the sample handling unit 1 are formed of, e.g., polycarbonate (PC), polymethylmethacrylate (PMMA), ultraviolet curable resin or the like, and are preferably formed of the same material. If the first plate member 2 and the second plate member 3 are thus formed of the same material, the surface charge of the first plate member 2 can be equal to that of the second plate member 3, so that the electroosmosis flow to a sample during electrophoresis can be uniform to cause the flow of the sample to be constant. In addition, if the first plate member 2 and the second plate member 3 are formed of the same material, when an adhesive is allowed to permeate a gap between the bonded surfaces 2a and 3a of the first and second plate members 2 and 3 due to capillarity, the behavior of the adhesive toward the first plate member 2 is the same as that toward the second plate member 3, so that the movement of the adhesive due to capillarity is smooth. Furthermore, the first plate member 2 is larger than the second plate member 3 so as to protrude from the side faces of the second plate member 3 by a predetermined width (e.g., by side walls 6a through 6d as described later).

The first plate member 2 has a substantially rectangular planar shape. The first plate member 2 has a first elongated linear fine groove (recessed portion) 4 in the substantially central portion of its top face (the bonded surface 2a serving as a first surface), and a second fine groove (recessed portion) 5 substantially perpendicular to the first fine groove 4. The first and second fine grooves 4 and 5 have a substantially square cross section (the length of one side is in the range of from 50 to 100 micrometers), and an overall length of a few centimeters. Around the fine grooves 4 and 5 of the first plate member 2, the bonded surface 2a is formed. From the edges of the first plate member 2, side walls 6a through 6d protrude for housing the second plate member 3 in a space surrounded by the side walls 6a through 6b.

The side walls 6a through 6d of the first plate member 2 have such a height that the side walls 6a through 6d protrude from the external surface 7 of the second plate member 3 when the second plate member 3 is bonded and fixed to the first plate member 2. The side walls 6a through 6d of the first plate member 2 are partially cut out. In the cut-out portions of the side walls 6a through 6d, elastically deformable holding members 8 through 13 are integrally formed independently of the side walls 6a through 6d. The holding members 8, 9, 11 and 12 are arranged on the sides of both end portions of the side walls 6a and 6c facing longitudinal side faces 14 and 15 of the second plate member 3. The holding members 8 and 9 on the side of one side wall 6a of the first plate member 2 face the holding members 12 and 11 on the side of the other side wall 6c of the first plate member 2. The holding members 10 and 13 are arranged so as to face the central portions of the side faces 16 and 17 substantially perpendicular to the side faces 14 and 15 of the second plate member 3.

As shown in FIG. 2, the holding members 8 through 13 have an elastically deformable support portion 18 vertically extending upwards from the first plate member 2, and a hook portion 21 inwardly protruding from the tip end portion of the support portion 18 to be engageable with the external surface (outside engaging portion 20) of the second plate member 3. The hook portion 21 has an inclined surface 23 for contacting and guiding a chamfered portion 22, which is formed on the edge of the side face of the second plate member 3, when the second plate member 3 is mounted on the first plate member 2 from top. The bottom face 24 of the hook portion 21 is designed to contact the outside engaging portion 20 of the second plate member 3 to press the second plate member 3 on the first plate member 2 so as to prevent the second plate member 3 from moving in a direction (upwards in FIG. 2) in which the second plate member 3 is peeled off from the first plate member 2. In such holding members 8 through 13, the inclined surface 23 of the hook portion 21 is pushed by the chamfered portion 22 of the second plate member 3 when the second plate member 3 is mounted on the first plate member 2 from top in FIG. 2, so that the support portion 18 is deformed by external force acting on the inclined surface 23 to allow the second plate member 3 to move toward the first plate member 2. Then, when the second plate member 3 is pushed into a predetermined portion on the first plate member, the support member 18 is designed to restore to the original attitude by its elasticity, so that the hook portion 21 engages the outside engaging portion 20 of the second plate member 3. Furthermore, if the top of each of the holding members 8 through 13 is designed so as not to protrude from the external surface 7 of the second plate member 3 and if the top of each of the side walls 6a through 6d is designed so as not to protrude from the external surface 7 of the second plate member 3, when a spotting device or the like moves along the external surface 7 of the second plate member 3, the movement of the spotting device or the like is not obstructed by the top of each of the side walls 6a through 6d and holding members 8 through 13, so that the ability of operation, such as spotting operation, is improved.

On the side of the bonded surface 2a of the first plate member 2, there are formed a plurality of inside holding members 26 and 27 which are hooked on the inside engaging portions 25 of the second plate member 3. The inside holding members 26 and 27 are arranged in the vicinity of the first fine groove 4 on both sides thereof so as to be symmetrical with respect to the first fine groove 4. That is, the bonded surface 2a on one side of the first fine groove 4 and the bonded surface 2a on the other side thereof are formed with the pair of inside holding members 26 and 27, respectively, which are arranged back to back and which are displaced from each other so as not to interfere with each other. Each of the inside holding members 26 and 27 substantially has the same shape as that of each of the above described holding members 8 through 13. Each of the inside holding members 26 and 27 has an elastically deformable support portion 28 protruding from the first plate member 2, and a hook portion 30 which is formed so as to protrude from the tip end portion of the support portion 28 to the side and which is hooked on the inside engaging portion 25 of the second plate member 3. The upper portion of the hook portion 30 is formed with an inclined surface 33 for contacting and guiding a chamfered portion 32, which is formed on the bottom end of a hole 31 of the second plate member 3, when the second plate member 3 is mounted on the first plate member 2 from top in FIG. 2.

If the inclined surface 33 of the hook portion 30 is pushed by the chamfered portion 32 of the second plate member 3, the support portion 28 is flexibly deformed to allow the inside holding members 26 and 27 to pass through the hole 31. Then, if the hook portion 30 passes through the hole 31 to mount the second plate member 3 on the first plate member 2 at a predetermined position, the support portion 28 restores to the original attitude, so that the hook portion 30 engages the inside engaging portion 25 of the second plate member 3. Then, the bottom surface 34 of the hook portion 30 presses the inside engaging portion 25 on the bonded surface 2a of the first plate member 2. As a result, the second plate member 3 is fixed at a position near the first fine groove 4 of the first plate member by means of the inside holding members 26 and 27. Furthermore, as shown in FIG. 2, the hook portion 30 is designed to push the bottom face of the inside engaging portion 25, which is a recessed portion formed in the upper open end of the hole 31. The inside holding members 26 and 27 are formed so that the top ends 26a and 27a thereof do not protrude from the external surface 7 of the second plate member 3.

On the surfaces (inside surfaces) of the side walls 6a through 6d of the first plate member 2 facing the side faces 14 through 17 of the second plate member 3, there are formed substantially semi-spherical protrusions 35 serving as positioning means for preventing the second plate member 3 from being displaced from the first plate member 2 (in X and Y directions in FIGS. 1 and 2). The protrusions 35 are arranged in the substantially central portion in longitudinal directions of the second plate member 3 substantially having the rectangular planar shape, and arranged in both end portions in lateral directions of the second plate member 3. Protrusions 36 similar to the protrusions 35 are formed on surfaces of the holding members 8 through 13 facing the second plate member 3. Thus, each of the four side faces 14 through 17 of the second plate member 3 is positioned so as to be well-balanced by the three protrusions 35 and 36 with respect to the first plate member 2. In the holding members 8 through 13, the protrusion 36 on the surface of the support portion 18 facing the second plate member 3 is designed to be pressed on the side faces 14 through 17 of the second plate member 3 by electrically deformation force of the support portion 18.

The second plate member 3 is a thin plate member which is housed in a space surrounded by the side walls 6a through 6d of the first plate member 2, and has a substantially rectangular planar shape. In the second plate member 3, through holes 37 for communicating both end portions of the first fine groove 4 of the first plate member 2 and both end portions of the second fine groove 5 thereof with outside environment are formed so as to face both end portions of the first fine groove 4 of the first plate member 2 and both end portions of the second fine groove 5 thereof.

The second plate member 3 has outside engaging portions 20 which are arranged so as to face the holding members 8 through 13 of the first plate member 2 and which are recessed so as to engage the hook portions 21 of the holding members 8 through 13. Each of the outside engaging portions 20 has a substantially rectangular planar shape as shown in FIG. 5, and is formed as a recessed portion having a rectangular sectional shape as shown in FIG. 6. The outside engaging portions 20 are formed by recessing a part of the external surface 7 of the second plate member 3, to form a part of the external surface 7. The second plate member 3 has the inside engaging portions 25 so as to correspond to the inside holding members 26 and 27 of the first plate member 2. The inside engaging portions 25 of the second plate member 3 are formed on both sides (on the right and left sides in FIG. 5) of the hole 31, which passes through the second plate member 3 in thickness directions, on the side of the external surface 7. The hole 31 has a rectangular shape so as to be capable of receiving therein the inside holding members 26 and 27 (see FIG. 5). Each of the inside engaging members 25 is a substantially rectangular recess on which the hook portions 30 of the inside holding members 26 and 27 are hooked. Each of the inside engaging members 25 has a rectangular planar shape as shown in FIG. 5, and is a recess having a rectangular sectional shape as shown in FIG. 6.

Figure 7:
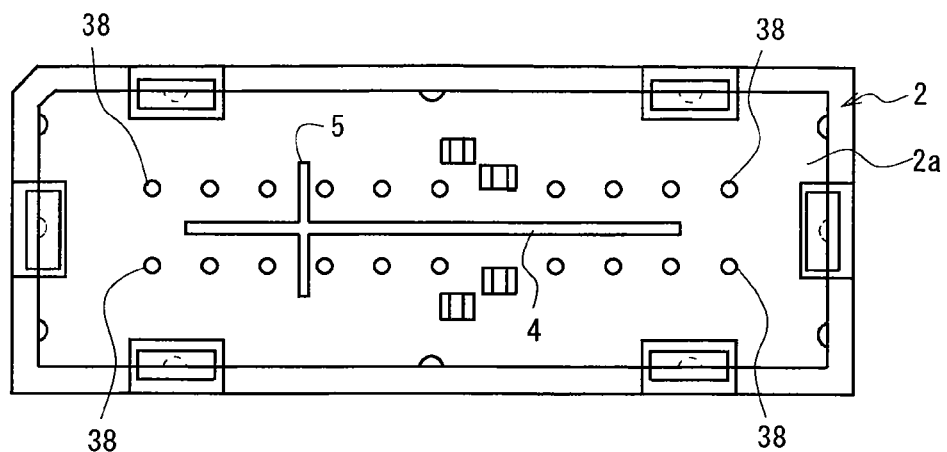
FIG. 7 is a plan view of a first plate member of another preferred embodiment of a sample handling unit according to the present invention.
Figure 8:
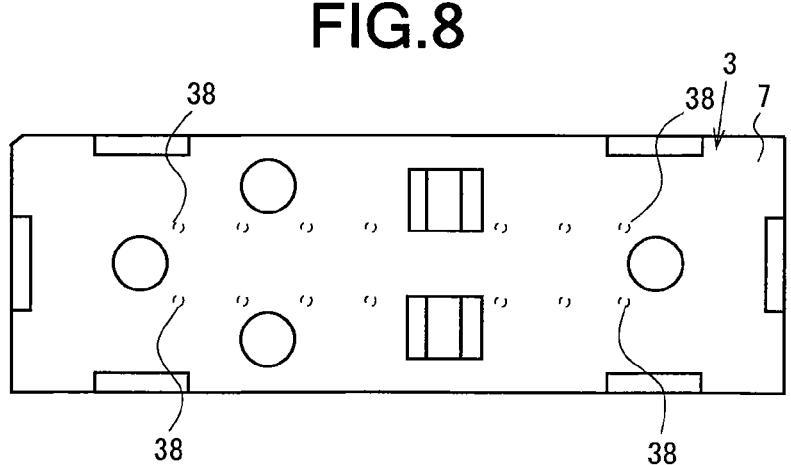
FIG. 8 is a plan view of a second plate member of another preferred embodiment of a sample handling unit according to the present invention.
Figure 9:
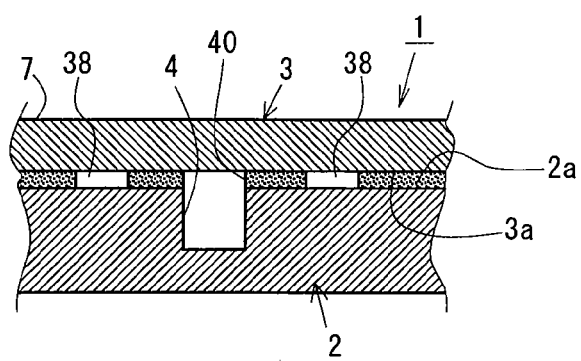
FIG. 9 is a sectional view of a part of a sample handling unit wherein the first plate member of FIG. 7 is bonded to the second plate member of FIG. 8.

At least one of the first and second plate members 2 and 3 is formed by injection molding. The surface of the cavity of an injection molding die is transferred to at least one of the bonded surfaces 2a and 3a of the first and second plate members 2 and 3 formed by injection molding, so that fine irregularities are formed thereon. As a result, even if the second plate member 3 is pressed on the first plate member 2, an adhesive can permeate fine gaps, which are formed between the bonded surface 2a of the first plate member 2 and the bonded surface 3a of the second plate member 3, due to capillarity. Moreover, if it is intended to more precisely form a gap between the bonded surface 2a of the first plate member 2 and the bonded surface 3a of the second plate member 3 to allow an adhesive 40 to more surely permeate the gap between the bonded surfaces 2a and 3a of the members 2 and 3 due to capillarity, a plurality of fine protrusions 38 are preferably formed on at least one of the bonded surface 2a of the first plate member 2 and the bonded surface 3a of the second plate member 3 as shown in FIGS. 7 through 9.

According to the above described constructions, if the second plate member 3 is housed in the space surrounded by the side walls 6a through 6d of the first plate member 2, the four side faces 14 through 17 of the second plate member 3 are guided by the protrusions 35 and 36 of the first plate member 2, and the second plate member 3 is mounted on the first plate member 2 at a predetermined position. Then, the hook portions 21 of the holding members 8 through 13 of the first plate member 2 engage the outside engaging portions 20 of the second plate member 3, and the hook portions 30 of the inside holding members 26 and 27 of the first plate member 2 engage the inside engaging portions 25 of the second plate member 3. Thus, the second plate member 3 is held by the first plate member 2.

Then, an adhesive is dripped from at least one of the four through holes 37 of the second plate member 3. At this time, the adhesive is dripped on the first plate member 2 so as not to flow into the first and second fine grooves 4 and 5. The adhesive permeates a fine gap between the bonded surfaces 2a and 3a of the first and second plate members 2 and 3, which face each other, due to capillarity, so that the first and second plate members 2 and 3 are surely bonded and fixed to each other. The bottom ends of the through holes 37 of the second plate member 3 bonded and fixed to the first plate member 2 are communicated with the end portions of the first and second fine grooves 4 and 5 to define storage portions 37a which are spaces capable of carrying out storage, injection and extraction of a sample or the like. Furthermore, the adhesive flowing due to capillarity does not enter the first and second fine grooves 4 and 5 in which the gap between the first and second plate members 2 and 3 abruptly increases. Therefore, the flow passage sectional area of the first and second fine grooves 4 and 5 can be substantially constant in longitudinal directions thereof. In addition to the through holes 37, adhesive injecting through holes (not shown) may be formed in the vicinity of the first and second fine grooves 4 and 5 in the second plate member 3 at regular intervals along the first and second fine grooves 4 and 5 for dripping an adhesive.

According to this preferred embodiment with the above described construction, the second plate member 3 is protected by the side walls 6a through 6d of the first plate member 2 to prevent external force from directly acting on the edges of the second plate member 3, and it is difficult for external force shearing the first and second plate members 2 and 3 in X and Y directions to act on the bonded surfaces 2a and 3a of the first and second plate members 2 and 3. Therefore, even if the sample handling unit 1 drops on the floor during handling or collides with another obstacle, the adhesive layer sealing the portions surrounding the first and second fine grooves 4 and 5 is not partially broken by cracks or the like, and the function of the fine grooves 4 and 5 as microchannels do not deteriorate. In addition, it is difficult for the bonded surfaces 2a and 3a of the first and second plate members 2 and 3 to be broken due to peeling.

According to this preferred embodiment, the protrusions 35 formed on the side walls 6a through 6d of the first plate member 2, and the protrusions 36 formed on the holding members 8 through 13 can position the second plate member 3 with respect to the first plate member 2 in X and Y directions, and can prevent the second plate member 3 from being displaced with respect to the first plate member 2 in X and Y directions. As a result, according to this preferred embodiment, the first and second plate members 2 and 3 can be precisely bonded to each other without the need of any assembling tools. In particular, when the first and second plate members 2 and 3 are bonded and fixed to each other while fine recessed portions (not shown) and so forth formed in the bonded surface 2a of the first plate member 2 are aligned with fine recessed portions (not shown) and so forth formed in the bonded surface 3a of the second plate member 3, it is possible to precisely and surely carry out assembly operation.

According to this preferred embodiment, the second plate member 3 is pressed on the first plate member 2 by the hook portions 21 of the holding members 8 through 13. Therefore, when the first and second plate members 2 and 3 are bonded and fixed to each other, the bonding operation of the first plate member 2 to the second plate member 3 can be easily and surely carried out without the need of any tools for clamping the first and second plate members 2 and 3.

According to this preferred embodiment, the second plate member 3 is pressed on the first plate member 2 by the hook portions 21 of the holding members 8 through 13 to be positioned and fixed with respect to the first plate member 2 in Z directions. Therefore, even if force in a direction (Z direction) for peeling the second plate member 3 off from the first plate member 2 is applied thereon, the holding members 8 through 13 can oppose the force. Therefore, there is not the possibility that the second plate member 3 is peeled off from the first plate member 2 to be damaged.

According to this preferred embodiment, the side faces 14 through 17 of the second plate member 3 facing each other are clamped by utilizing the elasticity of the support portions 18 of the holding members 8 through 13. Therefore, the second plate member 3 can be held without rattling the first plate member 2, so that the bonding operation of the second plate member 3 to the first plate member 2 can be more precisely and surely carried out. In addition, according to this preferred embodiment with such a construction, the side faces 14 through 17 of the second plate member 3 are elastically held by the holding members 8 through 13 of the first plate member 2. Therefore, even if shocks are given to the side walls 6a through 6d of the first plate member 2, the shocks are transmitted to the second plate member 3 while being relaxed by the elasticity of the holding members 8 through 13. As a result, it is difficult for impact force to act on the bonded surfaces 2a and 3a of the first and second plate members 2 and 3, so that it is possible to effectively prevent the sample handling unit 1 from being broken by the peeling of the bonded surfaces 2a and 3a of the first and second plate members 2 and 3 off from each other.

According to this preferred embodiment, the second plate member 3 can be pressed on the first plate member 2 by the inside holding members 26 and 27 formed in the vicinity of the first fine groove 4. Therefore, it is possible to prevent the central portion (the portion in the vicinity of the first fine groove 4) of the second plate member 3 from being deformed so as to rise. Thus, the gap between the bonded surfaces 2a and 3a of the first and second plate members 2 and 3 can be substantially constant in the whole area, so that the bonding operation of the first plate member 2 to the second plate member 3 can be more surely carried out. In particular, according to this preferred embodiment with such a construction, when an adhesive is allowed to permeate the fine gap between the bonded surfaces 2a and 3a of the first and second plate members 2 and 3 due to capillarity, the adhesive can uniformly and surely flow in the whole area of the bonded surfaces 2a and 3a.

According to this preferred embodiment, the side edges of the second plate member 3 can not only be held by the holding members 8 through 13, but the portions of the second plate member 3 in the vicinity of the first fine groove 4 can also be held by the inside holding members 26 and 27. Therefore, it is possible to more effectively oppose the force for peeling the second plate member 3 off from the first plate member 2.

In the sample handling unit 1 in this preferred embodiment, the side walls 6a through 6d of the first plate member 2 are formed so as to protrude upwardly from the external surface 7 of the second plate member 3. Therefore, the side walls 6a through 6d can surely protect the second plate member 3 from impact force and/or external force acting on the second plate member 3 from the side faces 14 through 17 thereof.

In the above described preferred embodiment, in order to prevent the assembly of the first and second plate members 2 and 3 from being erroneously carried out, a marker portion 41 is formed by obliquely cutting one of the four corners of the second plate member 3, and a fillet portion 42 engageable with the marker portion 41 is formed inside of the cross portion of the side wall 6a and side wall 6d of the first plate member 2.

While the sample handling unit 1 used as a capillary electrophoresis chip for carrying out a test in the field of biochemistry has been described as examples for convenience of explanation in the above described preferred embodiment, the present invention should not be limited thereto, but the sample handling unit 1 in the preferred embodiment may be widely applied to chemical tests in various fields other than the field of biochemistry, such as the fields of synthetic chemistry and analytical chemistry.

While the first and second fine grooves 4 and 5 have been formed in the first plate member 2 as an example in the above described preferred embodiment, the present invention should not be limited thereto, but the grooves may be formed in the bonded surface 3a of the second plate member 3, or in both of the bonded surfaces 2a and 3a of the first and second plate members 2 and 3.

While the side walls 6a through 6d of the first plate member 2 have been formed so as to protrude upwardly from the external surface 7 of the second plate member 3 in the sample handling unit 1 in the above described preferred embodiment, the present invention should not be limited thereto, but the side walls 6a through 6b may be formed so as not to protrude from the external surface 7 of the second plate member 3.

While the first and second plate members 2 and 3 have been bonded to each other with an adhesive in the sample handling unit 1 in the above described preferred embodiment, means for bonding the first and second plate members 2 and 3 to each other according to the present invention should not be limited to that in the above described preferred embodiment, but bonding means, such as laser welding, ultrasonic welding or heat welding, may be applied.

While the first and second plate members 2 and 3 have been formed of a synthetic resin as an example in the above described preferred embodiment, the present invention should not be limited thereto, but they may be formed of a glass or metal material. If the first and second plate members 2 and 3 are formed of a glass or metal material, means for bonding the members 2 and 3 to each other may be means suitable for bonding of the glass or metal material, in addition to the bonding means described as an example in the above described preferred embodiment.

While the adhesive has been allowed to permeate the gap between the bonded surface 2a of the first plate member 2 and the bonded surface 3a of the second plate member 3 due to capillarity after the mounting of the second plate member 3 on the first plate member 2 in the above described preferred embodiment, the present invention should not be limited thereto, but an adhesive may be previously applied on at least one of the bonded surface 2a of the first plate member 2 and the bonded surface 3a of the second plate member 3 before the second plate member 3 is mounted on the first plate member 2.

While the sectional shape of the first and second fine grooves 4 and 5 has been square in the above described preferred embodiment, the present invention should not be limited thereto, but the sectional shape may be another shape, such as semicircle, U-shape or substantially triangle.

According to the present invention, the number and position of the protrusions 35 and 36 should not be limited to those in the above described preferred embodiment shown in FIG. 1. The number and positions of the protrusions 35 and 36 may be suitably changed as long as the second plate member 3 can be positioned with respect to the first plate member 2 while it is possible to prevent the second plate member 3 from being displaced with respect to the first plate member 2. For example, only the protrusions 36 of the holding members 8 through 13 may be formed to omit the protrusions 35. Alternatively, only the protrusions 35 may be formed on the side walls 6a through 6d to omit the protrusions 36 of the holding members 8 through 13.

Figure 10:
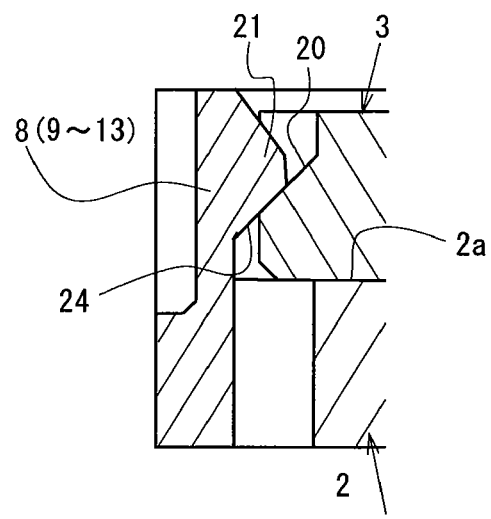
FIG. 10 is an enlarged sectional view of a part of a modified example of a sample handling unit in the preferred embodiment, which shows engagement of a holding member.

The bottom faces 24 of the hook portions 21 of the holding members 8 through 13, and the outside engaging portions 20 contacting the bottom faces 24, have been formed on a plane substantially in parallel to the bonded surface 2a in the above described preferred embodiment (see FIG. 2), the bottom faces 24 of the hook portions 21 of the holding members 8 through 13 and the outside engaging portions 20 may be inclined with respect to the bonded surface 2a to allow the bottom faces 24 of the hook portions 21 to depress the outside engaging portions 20 (inclined face) of the second plate member 3 obliquely downwards as shown in FIG. 10. With such a construction, the side faces 14 through 17 of the second plate member 3 facing each other can be clamped by the holding members 8 through 13, and the second plate member 3 can be pressed on the first plate member 2 by the holding members 8 through 13. As a result, it is possible to effectively prevent the second plate member 3 from being displaced with respect to the first plate member 2 by the holding members 8 through 13, so that it is possible to prevent the bonded surface 2a of the first plate member 2 from being peeled off from the bonded surface 3a of the second plate member 3.

Figure 11:
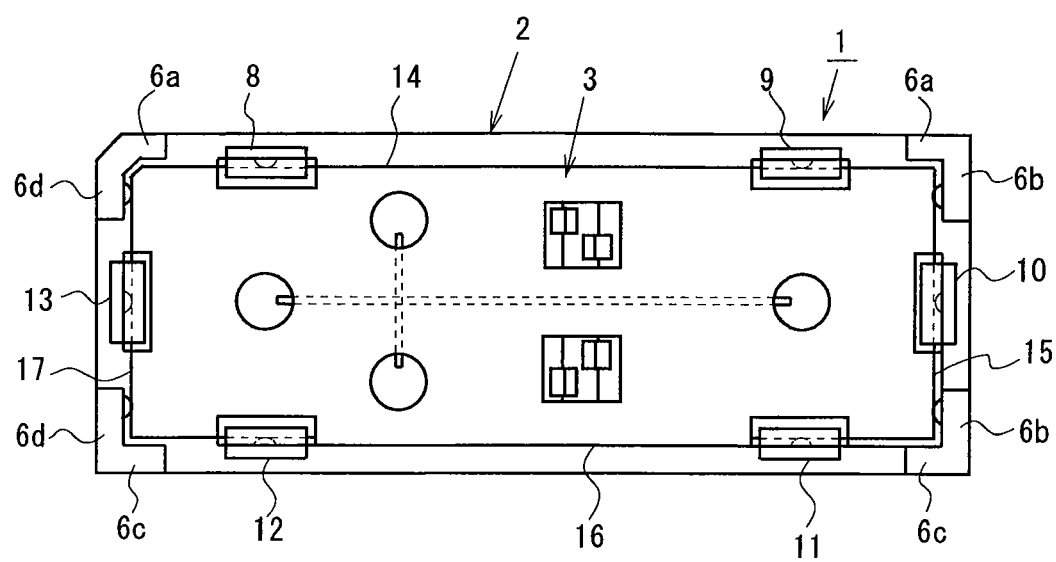
FIG. 11 is a plan view of another modified example of a sample handling unit in the preferred embodiment.

The side walls 6a through 6d of the first plate member 2 have been formed so as to substantially surround the whole area of the four side faces 14 through 17 of the second plate member 3 other than the holding members 8 through 13 in the above described preferred embodiment, the present invention should not be limited thereto, but the side walls 6a through 6d may be partially formed so as to protect the four corners of the second plate members 3 as shown in FIG. 11. Also with this construction, it is possible to prevent impact force from acting directly on the second plate member 3 when the dropping or the like of the sample handing unit 1 occurs, and it is difficult for external force to act on the bonded surfaces 2a and 3a of the first and second plate members 2 and 3, so that it is difficult for the bonded surfaces 2a and 3a of the first and second plate members 2 and 3 to be peeled off from each other.

Figure 12:
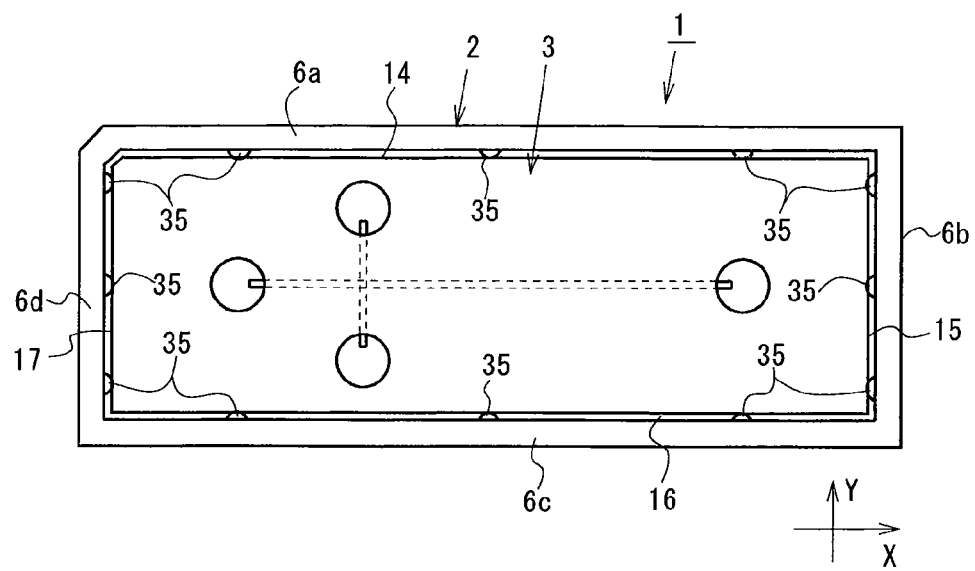
FIG. 12 is a plan view of another modified example of a sample handling unit in the preferred embodiment.

In the above described preferred embodiment, the holding members 8 through 13 and the inside holding members 26 and 27 may be omitted, and the side walls 6a through 6d of the first plate member 2 may be continuously formed so that each of the side walls 6a through 6d has three protrusions 35 for positioning both end portions and substantially central portion in longitudinal directions of each of the side faces 14 through 17 of the second plate member 3 as shown in FIG. 12.

Figure 13A:
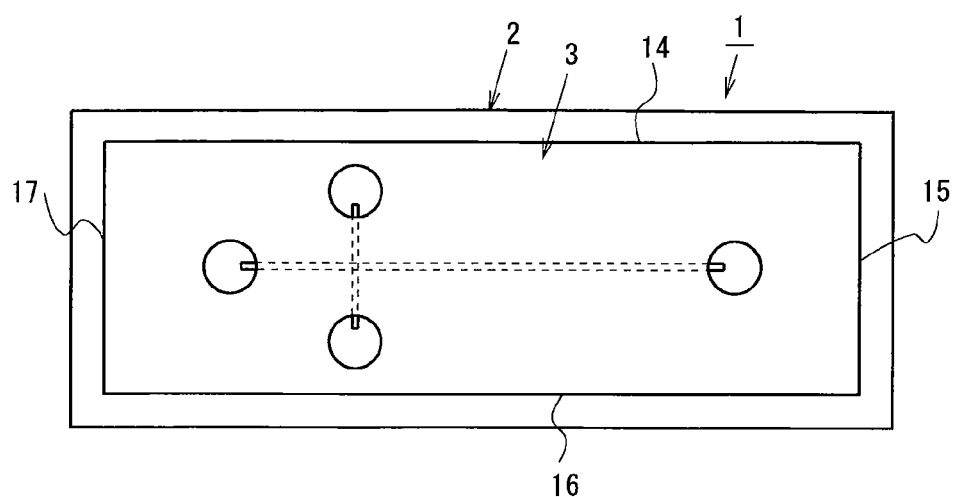
FIG. 13A is a plan view of another modified example of a sample handling unit in the preferred embodiment.
Figure 13B:
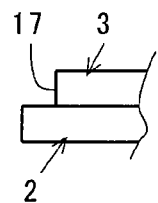
FIG. 13B is a side view of a part of the sample handling unit of FIG. 13A.

In the above described preferred embodiment, the holding members 8 through 13, the inside holding members 26 and 27, and the side walls 6a through 6d may be omitted, and the first plate member 2 may be larger than the second plate member 3 so as to protrude from the side faces 14 through 17 of the second plate member 3 as shown in FIGS. 13A and 13B. With such a construction, during fall or the like, the larger first plate member 2 is easy to collide with the floor or the like prior to the smaller plate member 3, and it is difficult for the first and second plate members 2 and 3 to simultaneously collide with the floor or the like, so that it is difficult for great force to act on the bonded surfaces 2a and 3a of the first and second plate members 2 and 3 to peel them off from each other.

Figure 14:
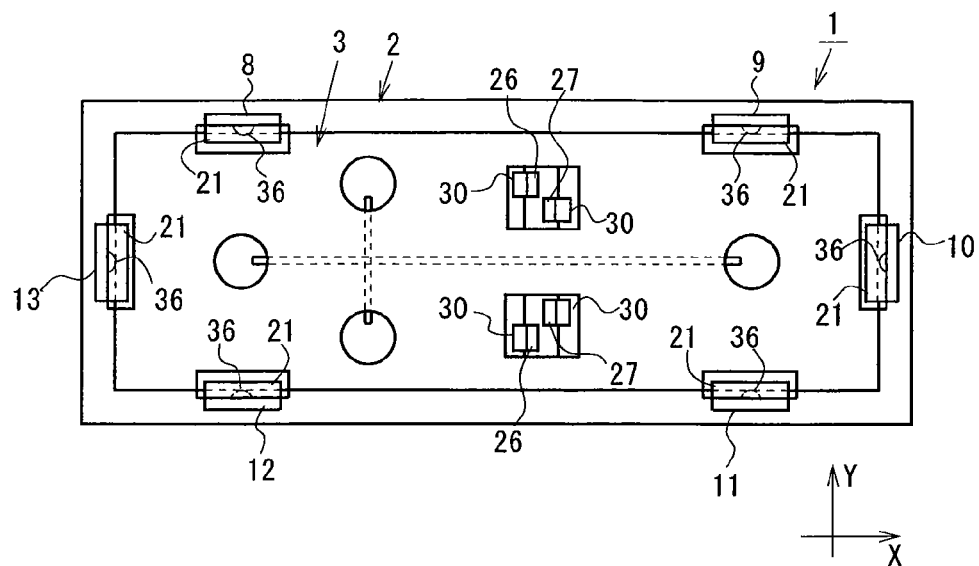
FIG. 14 is a plan view of another modified example of a sample handling unit in the preferred embodiment.
Figure 15:
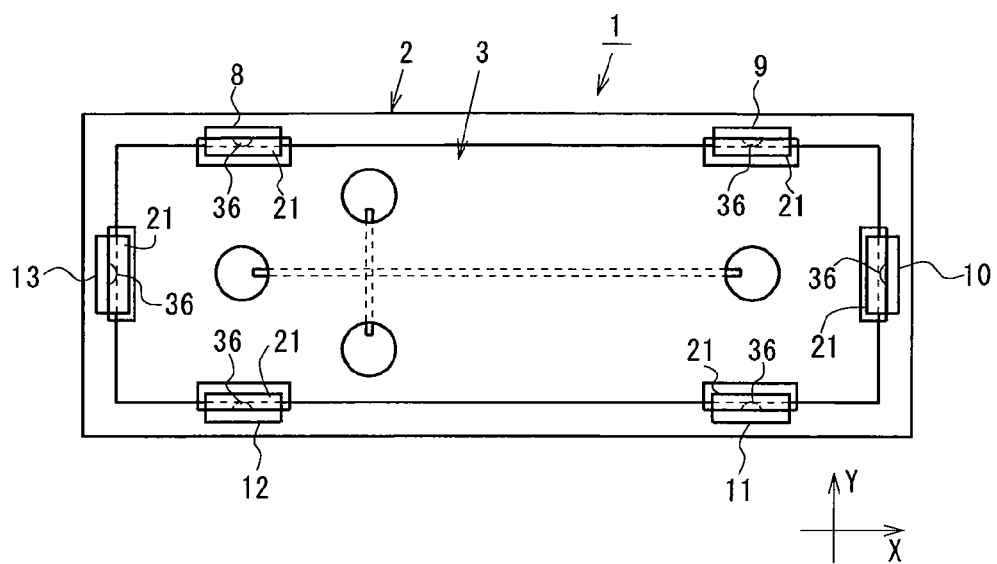
FIG. 15 is a plan view of another modified example of a sample handling unit in the preferred embodiment.

In the above described preferred embodiment, the side walls 6a through 6d may be omitted, and the second plate member 3 may be positioned and fixed on the first plate member 2 by the holding members 8 through 13 and inside holding members 26 and 27 as shown in FIG. 14. In the embodiment shown in FIG. 14, the holding members 8 through 13 may be omitted, and the second plate member 3 may be positioned and fixed on the first plate member 2 by only the inside holding members 26 and 27. Alternatively, as shown in FIG. 15, the second plate member 3 may be positioned and fixed on the first plate member 2 by the holding members 8 through 13. Furthermore, in the case of the embodiment shown in FIG. 14, the second plate member 3 is positioned with respect to the first plate member 2 in X and Y directions by means of the protrusions 36 of the holding members 8 through 13, and the second plate member 3 is positioned and fixed on the first plate member 2 in Z directions by means of the hook portions 21 of the holding members 8 through 13 and the hook portions 30 of the inside holding members 26 and 27. In the case of the embodiment shown in FIG. 15, the second plate member 3 is positioned with respect to the first plate member 2 in X and Y directions by means of the protrusions 36 of the holding members 8 through 13, and the second plate member 3 is positioned and fixed on the first plate member 2 in Z directions by means of the hook portions 21 of the holding members 8 through 13.

While the planar cross-shaped fine groove has been formed by the first and second fine grooves 4 and 5 in the first plate member 2 in the above described preferred embodiment, a fine groove having cross, Y-shape, curve or another complicated shape may be formed in the first plate member 2.

While the sample handling unit 1 has been formed by bonding the first thin plate member 2 and the second thin plate member 3 to each other in the above described preferred embodiment, the present invention should not be limited thereto, but a sample handling unit may be formed by bonding block pieces (first and second members) having any one of various shapes, not thin plate, to each other. Also in this case, recessed portions, such as fine grooves, for allowing the movement of the like of a sample are formed in the bonded surface of at least one of the block pieces.

In the above described preferred embodiment, one of the first plate member (first member) 2 and the second plate member (second member) 3 may be divided into a plurality of parts which are bonded to the other member.

While the fine grooves (the first fine groove 4 and the second fine groove 5) have been formed in the surface of one member (e.g., the first plate member 2) which is covered with another member (the second plate member 3) to form the sample handling unit 1 having a fine passage therein so as to allow a sample to move in the passage in the above described preferred embodiment, the present invention should not be limited thereto, but the invention may be applied to a sample handling unit which is formed by bonding at least two members and in which a sample can be moved, stored or held. For example, in addition to the sample handing unit wherein a sample is movable in the first and second fine grooves 4 and 5, the present invention can be applied to a sample handling unit wherein a plurality of wells capable of storing therein a sample are formed in the surface of one (substrate) of first and second members so as to be set in array and wherein a protective member (the other of the first and second members) is bonded to the surface of the substrate to cover the opening portions of the wells to protect the sample in the wells. In addition, according to the present invention, both of a microchannel (first recessed portion) for moving a sample, and a microwell (second recessed portion) for housing therein the sample may be formed in the bonded portion of the first plate member (first member) to the second plate member (second member).

Figure 16:
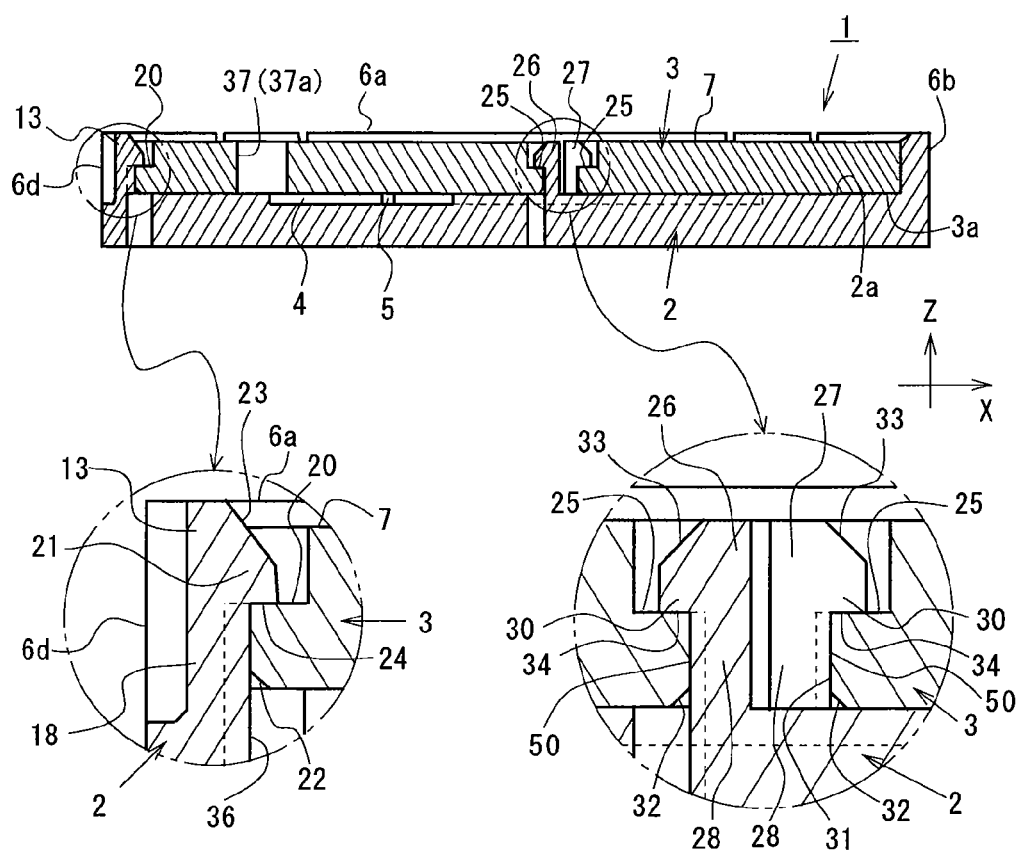
FIG. 16 is a sectional view of another modified example of a sample handling unit in the preferred embodiment, which corresponds to FIG. 2.

According to the present invention, as shown in FIG. 16, if a pair of protrusions 50 butting against the wall of the hole 31 are formed on the side faces of the support portions 28 of the inside holding members 26 and 27 and if the protrusions 50 are pressed on the wall of the hole 31 while the support portions 28 are elastically deformed, force in an opposite direction to the X direction in the figure acts on the wall of the hole 31 by the pair of protrusions 50. As a result, the inside holding members 26 and 27 protrude in the hole 31, and the second plate member 3 is held on the first plate member 2 by frictional force produced in the contact portion of the protrusions 50 of the inside holding members 26 and 27 with the wall face of the hole 31. According to such a modified example, the first and second plate members 2 and 3 can be integrated with each other by greater force in cooperation with the advantageous effects in the above described preferred embodiment.

While the hook portions 21 of the holding members 8 through 13 have engaged the outside engaging portions 20 of the second plate member 3 in the above described preferred embodiment, the present invention should not be limited thereto, but the hook portions 21 of the holding members 8 through 13 may be hooked directly on the external surface 7 of the second plate member 3 without forming the outside engaging portions 20 on the second plate member 3. Thus, it is not required to recess a part of the external surface 7 of the second plate member 3 to form the outside engaging portions 20.

According to the present invention, for example, in FIG. 1, the second plate member 3 may be pressed on the side wall 6b of the first plate member 2 by the holding member 13, and the second plate member 3 may be clamped by the holding member 13 and side wall 6b to be held on the first plate member 2. Even if the second plate member 3 is thus held by the holding members 8 through 13 and the side walls 6a through 6d of the first plate member 2 facing the holding members 8 through 13, it is possible to effectively prevent the bonded surfaces of the first and second plate members 2 and 3 from being peeled off from each other.

As described above, according to the present invention, in a sample handling unit formed by bonding first and second members to each other, it is difficult for external force to act in a direction in which the first and second members are peeled off from each other. Therefore, it is possible to effectively prevent the sample handling unit from being broken by the peeling of the bonded surfaces of the first and second members off from each other, and it is possible to effectively prevent desired functions from deteriorating in accordance with the partial breakage of the bonded surfaces of the first and second members.

Referring to the accompanying drawings, particularly to FIGS. 17A through 25, the preferred embodiments of a microfluidic device according to the present invention will be described below in detail.

First Preferred Embodiment

Figures 17A, 17B:
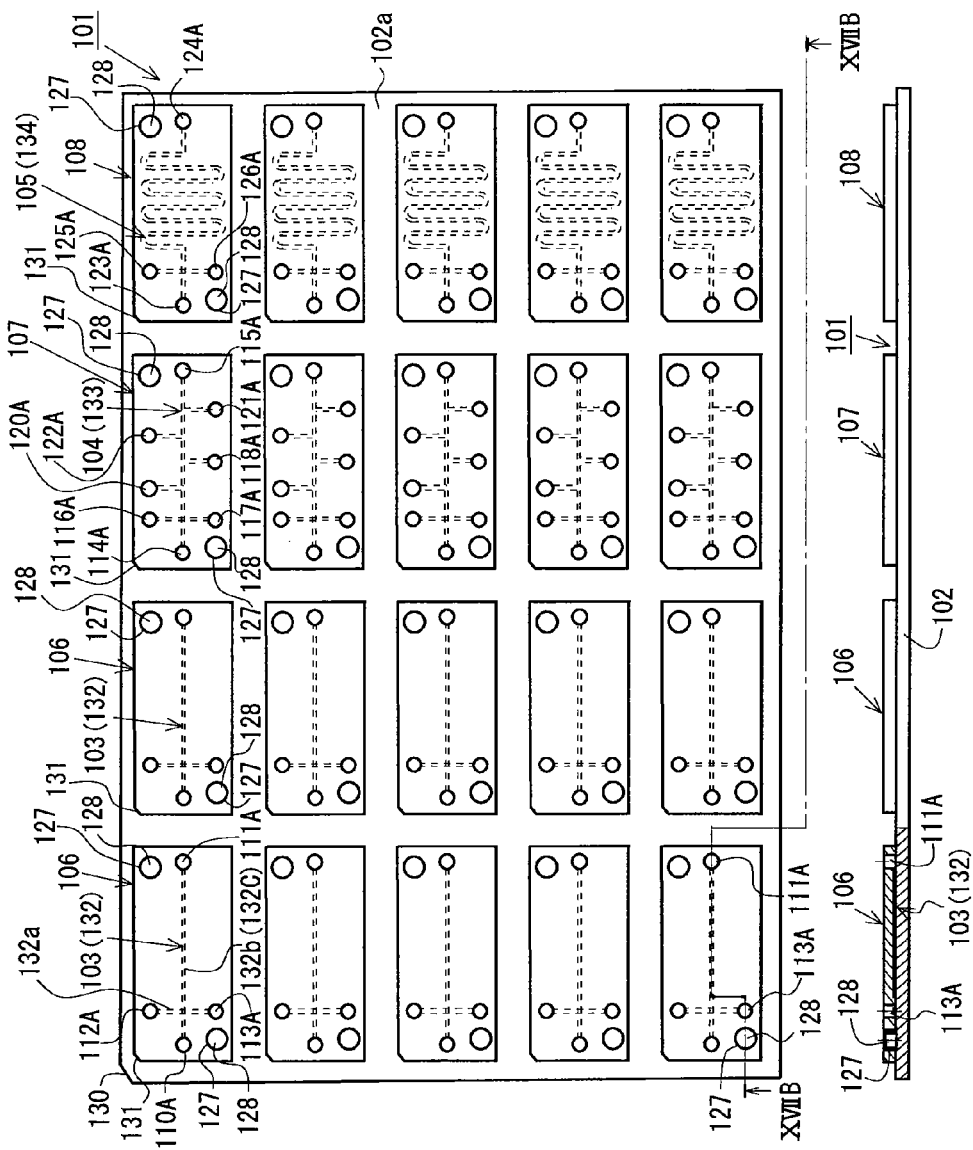
FIG. 17A is a plan view of the first preferred embodiment of a microfluidic device according to the present invention.
FIG. 17B is a partially sectional side view of the microfluidic device taken along line XVIIB-XVIIB of FIG. 17A.

FIGS. 17A and 17B show the first preferred embodiment of a microfluidic device 101 according to the present invention. FIG. 17A is a plan view of the microfluidic device 101, and FIG. 17B is a partially sectional side of the microfluidic device 101 view taken along line XVIIB-XVIIB of FIG. 17A.

As shown in FIGS. 17A and 17B, three kinds of microchips 106, 107 and 108 having fine grooves (recessed portions) 103, 104 and 105 having different shapes are arranged on the top face of a plate-like base member 102 so as to be set in array. That is, as shown in FIG. 17A, in a substantially left half region on the base member 102, ten microchips 106 of the first kind are arranged in two columns (first and second columns). In a substantially right half region on the base member 102, five microchips 107 of the second kind are arranged in the third column, and five microchips 108 of the third kind are arranged in the fourth column which the rightmost column on the base member 102. The base member 102 is associated with the microchips 106 through 108 of the first through third kinds arranged on the base member 102 for forming the microfluidic device 101.

In this preferred embodiment, the base member 102 and the microchips 106 through 108 of the first through third kinds are formed by injection-molding a resin material, such as polycarbonate (PC) or polymethylmethacrylate (PMMA). Furthermore, the material of the base member 102 and microchips 106 through 108 of the first through third kinds should not be limited to the above described resin materials, but they may be formed of a polymeric material, such as polydimethylsiloxane (PDMS), an ultraviolet curable resin, an inorganic material, such as a glass material, or a metal material.

Figure 18C:
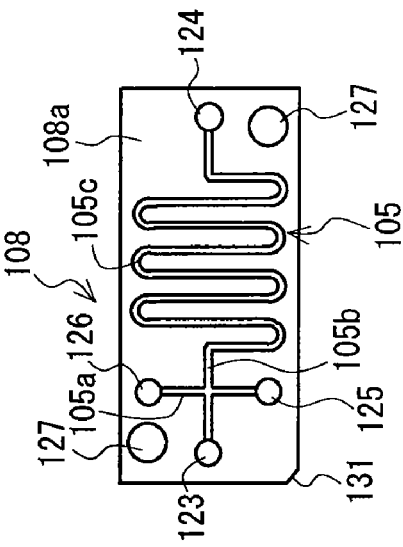
Figure 18B:
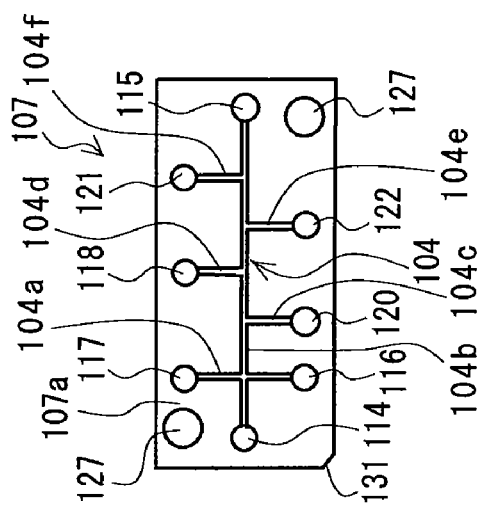
Figure 18A:
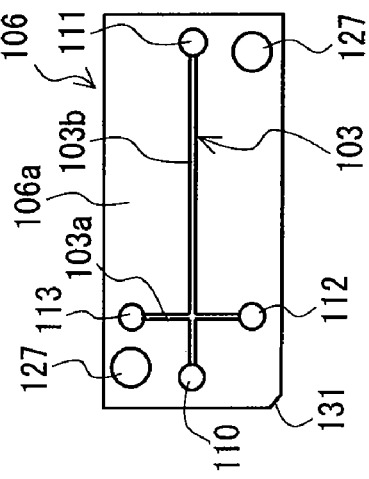

As shown in FIG. 18A, the microchip 106 of the first kind has a substantially rectangular planar shape. In one surface 106a of the microchip 106, there is formed a cross-shaped fine groove 103 comprising a fine groove 103a linearly extending in lateral directions of the microchip 106, and a fine groove 103b linearly extending in directions perpendicular to the fine groove 103a. In both end portions of each of the fine grooves 103a and 103b, through holes 110 through 113 are formed.

As shown in FIG. 18B, the microchip 107 of the second kind has a substantially rectangular planar shape. In one surface 107a of the microchip 107, there is formed a fine groove 104 comprising a fine groove 104a linearly extending in lateral directions of the microchip 107, a fine groove 104b linearly extending in directions perpendicular to the fine groove 104a, and fine grooves 104c through 104f which are first through fourth sub-grooves sequentially communicated with the fine groove 104b downstream of the fine groove 104a (on the right side of the fine groove 104a in the figure). In both end portions of each of the fine grooves 104a and 104b and in the opposite end portions of the fine grooves 104c through 104f to the end portions communicated with the fine groove 104b, through holes 114 through 122 are formed. Furthermore, the microchip 107 of the second kind has the same size as that of the microchip 106 of the first kind.

As shown in FIG. 18C, the microchip 108 of the third kind has a substantially rectangular planar shape. In one surface 108a of the microchip 108, there is formed a fine groove 105 comprising a fine groove 105a linearly extending in lateral directions of the microchip 108, and a fine groove 105b perpendicular to the fine groove 105a. The fine groove 105b has a meander portion 105c meandering downstream of the fine groove 105b (on the right side of the fine groove 105a) for ensuring a sufficient length for mixing, reaction, analysis or the like. In both end portions of each of the fine grooves 105a and 105b, through holes 123 through 126 are formed. Furthermore, the microchip 108 of the third kind has the same size as that of the microchip 106 of the first kind.

Each of the fine grooves 103a, 103b, 104a through 104f, 105a and 105b forming the fine grooves 103, 104 and 105 in this preferred embodiment has a width and depth of 50 micrometers, but the width and depth should not be limited thereto. The width and depth of the fine groove may be suitably set in the range of from 1 to 10000 micrometers in accordance with the kind of a specimen moving in a passage, which is formed by closing the opening portion of each of the fine grooves 103a, 103b, 104a through 104f, 105a and 105b as described later, and the kind of a fluid in the passage, or in accordance with the driving force or the like of the specimen or fluid.

As shown in FIGS. 17A through 18C, after the surface (surface 106a, 107a or 108a) of each of the microchips 106 through 108 having the fine groove 103, 104 or 105 is arranged so as to face the base member 102, a pair of positioning holes 127 formed in the corner portions in directions of a diagonal line of each of the microchips 106 through 108 are engaged with a pair of positioning pins 128 formed so as to protrude from the base member 102, and each of the microchips 106 through 108 is bonded to the base member 102, so that the opening of each of the fine grooves 103 through 105 is closed by the surface 102a of the base member 102. Thus, passages 132 through 134 are formed, and one end portion of each of the through holes 110 through 126 is closed to form reservoirs (storage portions) 110A through 126A. Furthermore, the positioning holes 127 of the microchips 106 through 108 are associated with the positioning pins 128 of the base member 102 for forming a positioning means for mounting the microchips 106 through 108 on the base member 102 while positioning the microchips 106 through 108 with respect to the base member 102. The microchips 106 through 108 may be integrated with the base member 102 by a fixing method (e.g., ultrasonic welding) other than adhesion.

For example, in the microchip 106 of the first kind of the microchips 106 through 108 with such a construction, an electrophoretic solution is injected into the passage 132 from any one of the reservoirs 110A through 113A, and a sample is injected from any one of the reservoirs 112A and 113A in the end portions of the shorter passage 132a. Thereafter, a high voltage is applied between both end portions of the passage 132a crossing the longer passage 132b. Thus, the sample migrates in the passage 132a toward the cross portion in which the passage 132a crosses the passage 132b. Then, when the sample migrates to the cross portion in which the passage 132a crosses the passage 132b, a migration voltage is applied between both end portions of the longer passage 132b. Thus, a very small amount of sample in the cross portion, in which the passages 132a and 132b cross, migrates in the analyzing passage 132c. Therefore, a detector (not shown), such as a fluorophotometer or an ultraviolet-visible light spectrophotometer, is previously arranged at an appropriate position in the analyzing passage 132c so as to be capable of analyzing the sample migrating in the analyzing passage 132c.

It is considered that means for forming a patterned electrode (not shown) on the bonded surface of the microchips 106 to the base member 102 to allow a current to pass through the electrode to simultaneously apply a voltage to a column of microchips 106 is used as means for applying a voltage between both end portions of each of the passages 132a and 132b. Alternatively, means for suitably inserting an electrode into each of the reservoirs 110A through 113A to apply a voltage may be used. In the microchip 107 of the second kind, a sample in the passage 133 can migrate by applying a voltage to any one of the reservoirs 114A through 122A. In the microchip 108 of the third kind, a sample in the passage 134 can migrate by applying a voltage to any one of the reservoirs 123A through 126A.

In the microfluidic device 101 with the above described construction, after the base member 102 and various microchips 106 through 108 are separately formed, microchips 106 through 108 of kinds necessary for intended purpose, such as analysis, can be selected to be suitably combined to be positioned and fixed on the base member 102. Therefore, according to this preferred embodiment, when the microchips 106 through 108 are formed by injection molding, the size of an injection molding die can be decreased, and the die can be easily worked, so that the cost of producing the die can be decreased. Since the shape of the base member 102 is also simple, the cost of producing the base member 102 can be decreased. As a result, the microfluidic device 101 in this preferred embodiment can be more inexpensively produced than a conventional device wherein a large number of microchannels are formed in a single plate so as to be set in array. In addition, according to this preferred embodiment, the components of the microfluidic device 101 can be miniaturized, so that it is possible to reduce the rate of occurrence of defective units to improve production efficiency to reduce the price of products.

In the microfluidic device 101 in this preferred embodiment, various microchips 106 through 108 having fine grooves 103 through 105 having different shapes can be suitably combined in accordance with intended purpose, such as analysis, so that it is possible to simply carry out analysis or the like for general purpose.

In FIG. 17A, the upper-left corner portion 130 of the base member 102 is chamfered, and the upper-left corner portion 131 of each of the microchips 106 through 108 is chamfered. Thus, it is possible to prevent each of the microchips 106 through 108 from being mounted on the base member 102 in an erroneous attitude.

While the sample has migrated by electrophoresis in the passages 132 through 134 of the microchips 106 through 108 in this preferred embodiment, the present invention should not be limited thereto. A sample may be moved by utilizing capillarity, or a portion for moving a sample due to capillarity may be combined with a portion for moving a sample by electrophoresis. Alternatively, a sample may be moved by utilizing a pressure difference, such as positive or negative pressure, as driving force.

While the microchips 106 through 108 of the first through third kinds have been used as an example in the preferred embodiment, plural kinds of microchips having fine grooves (microchannels) having a shape other than that of the fine grooves 103 through 105, and/or plural kinds of microchips having a large number of wells (fine recessed portions) may be combined to be formed on the base member 102.

While the positioning holes 127 have been formed in the microchips 106 through 108 and the positioning protrusions 128 have been formed on the base member 102 in the preferred embodiment, the present invention should not be limited thereto. Positioning protrusions may be formed on the microchips 106 through 108, and positioning holes engageable with the positioning protrusions may be formed in the base member 102.

The fine grooves 103 through 105 of the microchips 106 through 108 may be previously closed by a film or the like to be arranged on the base member 102 without closing the fine grooves 103 through 105 by the base member 102.

In the preferred embodiment, storage portions (not shown) serving as sample storages having an increased flow passage sectional area may be suitably formed in the middle of each of the passages 132, 133 and 134.

Second Preferred Embodiment

Figures 19A, 19B:
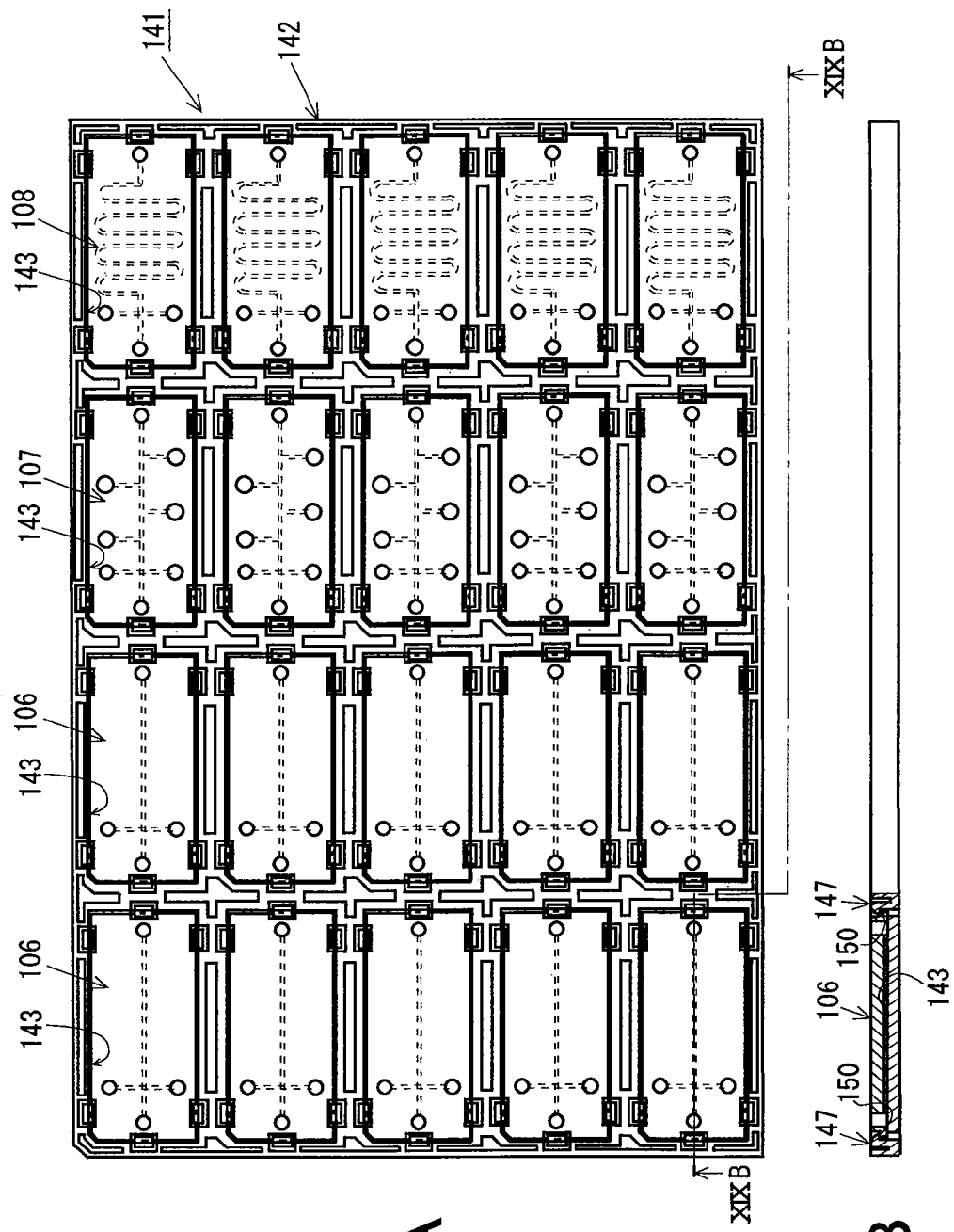
FIG. 19A is a plan view of the second preferred embodiment of a microfluidic device according to the present invention.
FIG. 19B is a partially sectional side view of the microfluidic device taken along line XIXB-XIXB of FIG. 19A.
Figure 20:
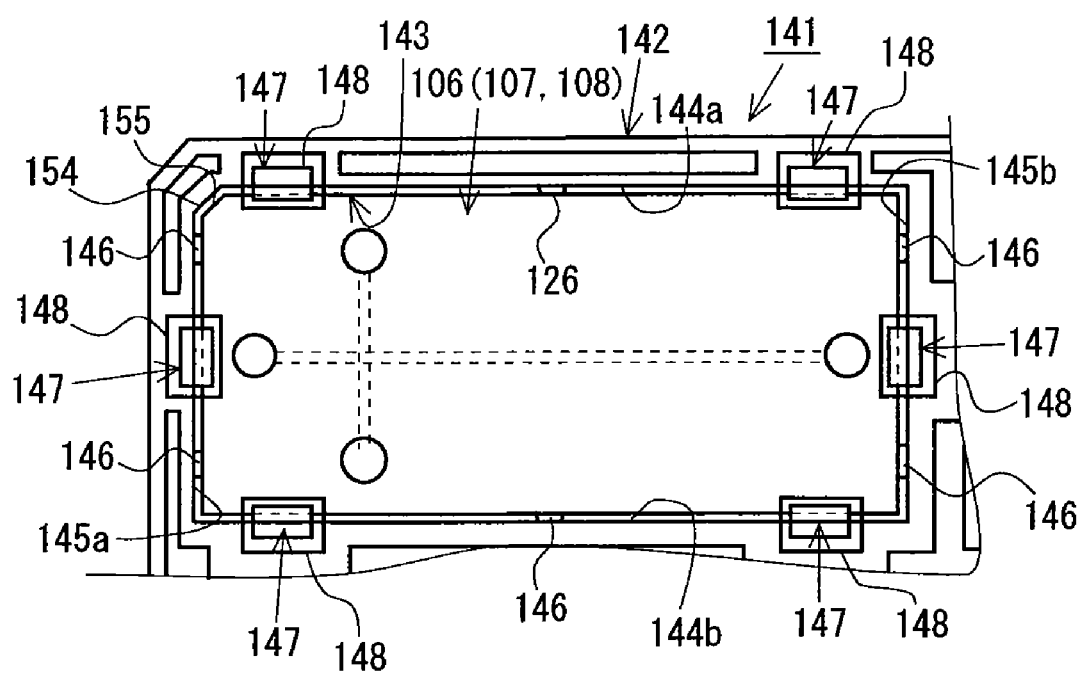
FIG. 20 is an enlarged view of a part of FIG. 19A.
Figure 21:
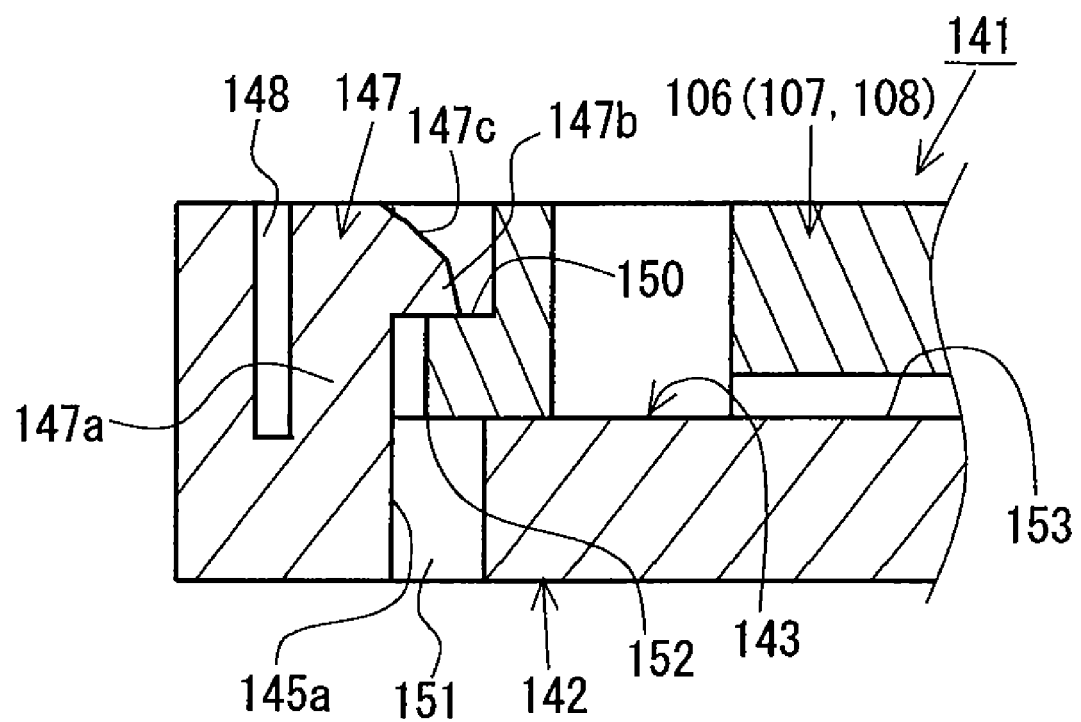
FIG. 21 is an enlarged sectional view of a part of FIG. 19B.

FIGS. 19A through 21 show the second preferred embodiment of a microfluidic device 141 according to the present invention. FIG. 19A is a plan view of the microfluidic device 141 in this preferred embodiment, and FIG. 19B is a partially sectional side view of the microfluidic device 141 taken along line XIXB-XIXB of FIG. 19A. FIG. 20 is an enlarged view of a part of FIG. 19A, and FIG. 21 is an enlarged sectional view of a part of FIG. 19A.

As shown in these figures, twenty microchip housing recesses 143 for detachably housing therein microchips 106 through 108 are formed in the top face of a plate-like base member 142 so as to be arranged in the form of an array of four columns×five rows. The microchips 106 of the first kind are housed in the microchip housing recesses 143 of two columns (the first and second columns), and the microchips 107 of the second kind are housed in the microchip housing recesses 143 of the third column. The microchips 108 of the third kind are housed in the microchip housing recesses 143 of the fourth column. Thus, the base member 142 is associated with the microchips 106 through 108 of the first through third kinds for forming the microfluidic device 141.

In this second preferred embodiment, if the microchips 106 through 108 are housed in the microchip housing recesses 143, the microchips 106 through 108 are positioned with respect to the base member 142 by positioning protrusions 146 which are formed on side walls 144a, 144b, 145a and 145b of each of the microchip housing recesses 143. Therefore, the microchips 106 through 108 are not formed with the positioning holes 127 in the first preferred embodiment, and the base member 142 is not formed with the positioning pins 128 in the first preferred embodiment (see FIGS. 19A, 19B and 20). In the second preferred embodiment, the microchips 106 through 108 may be formed of the same material as that in the first preferred embodiment using the same working method as that in the first preferred embodiment. On the other hand, the base member 142 is precisely formed by injection molding. Furthermore, in this preferred embodiment, the positioning protrusions 146 of the microchip housing recesses 143 function as means for positioning the microchips 106 through 108 on the base member 142.

The planar size of each of the microchip housing recesses 143 is larger than that of each of the microchips 106 through 108. Each of the microchip housing recesses 143 has chip pressing claws 147 on the sides of both end portions of each of a pair of longer facing edge portions (side walls 144a and 144b) thereof, and in the substantially central portions of each of a pair of shorter facing edge portions (side walls 145a and 145b) thereof. In addition, each of the microchip housing recesses 143 has positioning protrusions 146, which are engageable with the side faces of the microchips 106 through 108 via a slight gap, in the substantially central portion of each of the pair of longer facing edge portions (the side walls 144a and 144b) in longitudinal directions, and on the sides of both end portions of each of the pair of shorter facing edge portions (the side walls 145a and 145b) in longitudinal directions.

As shown in FIG. 21, each of the chip pressing claws 147 comprises an upright wall 147a which is elastically deformable independently of other portions of the base member 142, and a protruding portion 147b which protrudes from a side face of the upper portion of the upright wall 147a toward a corresponding one of the microchip housing recesses 143. The upper portion of the protruding portion 147b is formed with a chamfered portion 147c which is obliquely cut in the vicinity of the tip of the protruding portion 147b. If the upper portion of the protruding portion 147b is thus formed with the chamfered portion 147c, the edge portion 152 of the bottom face of each of the microchips 106 through 108 can press a corresponding one of the chip pressing claws 147 to expand a corresponding one of the microchip housing recesses 143, so that a corresponding one of the microchips 106 through 108 can be easily inserted into the corresponding one of the microchip housing recesses 143. On the sides of the back face and both side faces of each of the chip pressing claws 147, a deeper groove 148 than the depth of a corresponding one of the microchip housing recesses 143 is formed so as to surround the corresponding one of the chip pressing claws 147 (see FIG. 20). With such a construction, each of the chip pressing claws 147 is easy to be flexibly deformed toward its back face which is opposite to the corresponding one of the microchip housing recesses 143, so that the operation for attaching and detaching each of the microchips 106 through 108 to and from the corresponding one of the microchip housing recesses 143.

In a portion of each of the microchips 106 through 108 facing the corresponding one of the chip pressing claws 147, an engaging recess 150 engageable with the protruding portion 147b of the corresponding one of the chip pressing claws 147 is formed so as to be cut out.

As shown in FIG. 21, a portion which is arranged in each of the microchip housing recesses 143 and which is positioned directly below the protruding portion 147b of the corresponding one of the chip pressing claws 147, is communicated with the bottom face of the base member 142 via a hole 151. Thus, the base member 142 can be formed by injection molding regardless of the presence of the under-cut portion (a portion in which the protruding portion 147b is formed) of each of the chip pressing claws 147.

With such a construction, when each of the microchips 106 through 108 is intended to be mounted in a corresponding one of the microchip housing recesses 143, the edge portion 152 of the bottom face of a corresponding one of the microchips 106 through 108 first contacts the chamfered portion 147c of a corresponding one of the chip pressing claws 147, so that the corresponding one of the microchips 106 through 108 enters the corresponding one of the microchip housing recesses 143 while the corresponding one of the microchips 106 through 108 presses and flexibly deforms the corresponding one of the chip pressing claws 147. Then, when the corresponding one of the microchips 106 through 108 reaches the bottom face 153 of the corresponding one of the microchip housing recesses 143, the corresponding one of the chip pressing claws 147 elastically restores to its original attitude, so that the protruding portion 147b of the corresponding one of the chip pressing claws 147 engages the engaging recess 150 of the corresponding one of the microchips 106 through 108. Thus, it is possible to prevent the corresponding one of the microchips 106 through 108 from disengaging from the corresponding one of the microchip housing recesses 143, so that the corresponding one of the microchips 106 through 108 can be held on the base member 142.

On the other hand, when the microchips 106 through 108 are intended to be detached from the microchip housing recesses 143, all of the chip pressing claws 147 are simultaneously pressed to be open by an exclusive chip detaching tool (not shown) and the microchips 106 through 108 are grasped. Then, while all of the chip pressing claws 147 are pressed to be open by the chip detaching tool, the microchips 106 through 108 are taken out. Thus, the microchips 106 through 108 can be detached from the base member 142.

In such a microfluidic device 141 in this preferred embodiment, after the base member 142 and the microchips 106 through 108 of plural kinds are separately formed, the microchips 106 through 108 of kinds necessary for the base member 142 are selected, and the microchips 106 through 108 of the selected kinds can be suitably combined to be mounted in the microchip housing recesses 143 of the base member 142. Therefore, according to this preferred embodiment, if the microchips 106 through 108 are formed by injection molding, the injection molding die can be miniaturized and can be easily worked, so that the cost of producing the die can be reduced. In addition, since the base member 142 can be easily formed by injection molding, working costs can be reduced. As a result, the microfluidic device 141 in this preferred embodiment can be more inexpensively produced than a conventional device wherein a large number of microchannels are formed in a single plate so as to be set in array.

In the microfluidic device 141 in this preferred embodiment, the microchips 106 through 108 can be detachably mounted in the microchip housing recesses 143. Therefore, various microchips 106 through 108 having fine grooves 103 through 105 having different shapes can be suitably combined in accordance with intended purpose, such as analysis, so that it is possible to simply carry out analysis for general purpose.

Furthermore, in FIG. 20, a fillet portion 154 is formed in the upper-left corner portion of each of the microchip housing recesses 143 of the base member 142, and a chambered portion 155 engageable with the fillet portion 154 of a corresponding one of the microchip housing recesses 143 is formed in the upper-left corner portion of each of the microchips 106 through 108. Thus, it is possible to prevent each of the microchips 106 through 108 from being mounted on the base member 142 in an erroneous attitude.

In this preferred embodiment, the microchips 106 through 108 are held on the base member 142 by means of the chip pressing claws 47. Therefore, even if the microfluidic device 141 drops onto the floor or the like to receive shocks, it is possible to prevent the microchips 106 through 108 from being detached from the base member 142 to fly over the floor or the like. At this point, in the case of a microfluidic device where microchips are only bonded and fixed to a base member, if the microfluidic device drops onto the floor or the like, the microchips are peeled off from the base member by shocks, so that there is the possibility that the microchips are detached from the base member to fly over the floor or the like.

While the engaging recesses 150 formed in the microchips 106 through 108 have been designed to engage the chip pressing claws 147 formed on the base member 142 so that the microchips 106 through 108 are held on the base member 142 in this preferred embodiment, the external surfaces of the microchips 106 through 108 may be directly pressed and held by the chip pressing claws 147.

In this preferred embodiment, the protruding portions 147*b* of the chip pressing claws 147 are preferably pressed on the microchips 106 through 108 by utilizing elastic force caused by the flexible deformation of the chip pressing claws 147, so that the microchips 106 through 108 are surely held on the base member 142 by the elastic force of the chip pressing claws 147. Thus, it is possible to prevent the microchips 106 through 108 from being dislocated in the microchip housing recesses 143 by force acting on the contact surfaces of the chip pressing claws 147 to the engaging recesses 150.

In this preferred embodiment, the fine grooves 103 through 105 of the microchips 106 through 108 shown in FIG. 18A though 18C previously closed by another member (e.g., a thin plate member or film) other than the base member 142 may be detachably attached on the base member 142 without closing the fine grooves 103 through 105 by the base member 142.

Third Preferred Embodiment

Figure 22:
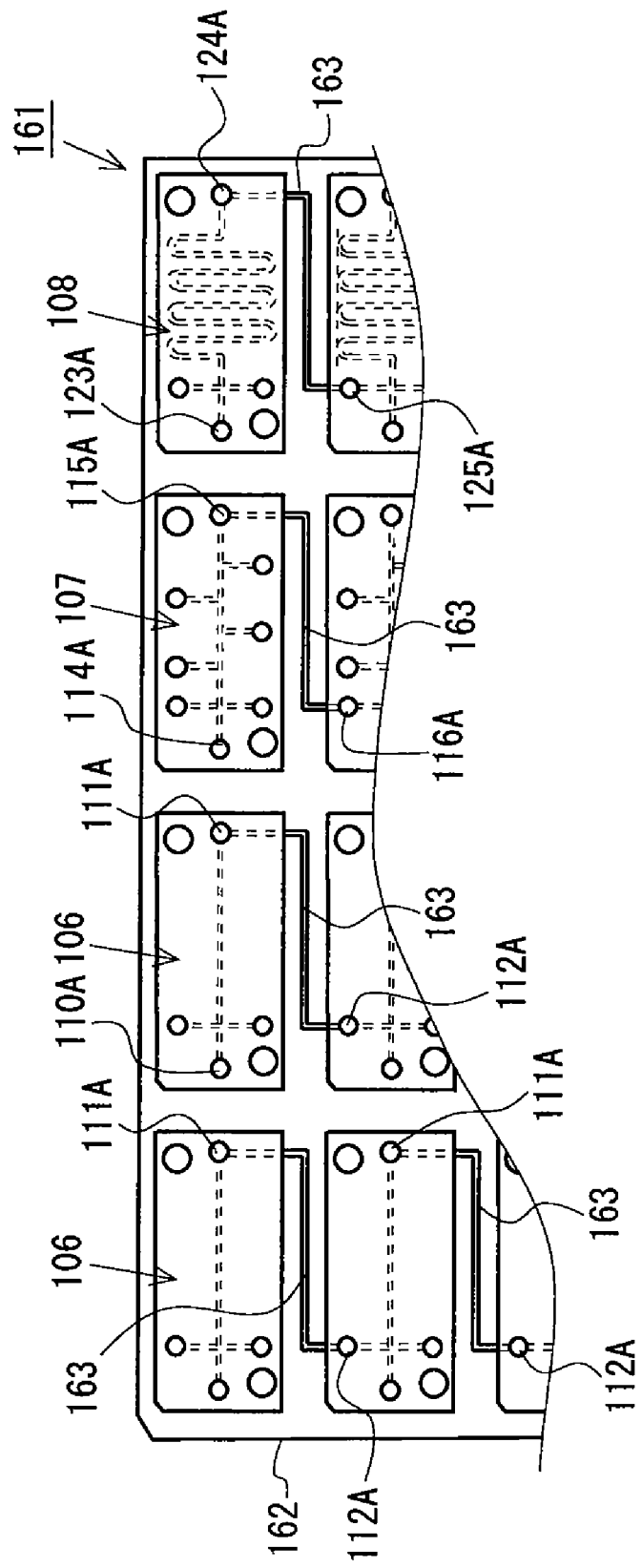
FIG. 22 is a plan view of a part of the third preferred embodiment of a microfluidic device according to the present invention.

FIG. 22 shows the third preferred embodiment of a microfluidic device 161 according to the present invention. In this preferred embodiment, one reservoir 111A (115A, 124A) of adjacent two of microchips 106 through 108 is communicated with the other reservoir 112A (116A, 125A) of the adjacent two of the microchips 106 through 108 via a communication passage 163 formed in a base member 162.

With such a construction, after a first analysis is carried out by the first microchip 106 (107, 108), a sample used in the first analysis can be fed to the second microchip 106 (107, 108) via the communication passage 163 in the base member 162 to be subsequently mixed with another sample or reagent to carry out a second analysis. Thus, the sample can be continuously analyzed by the microchips 106 (107, 108) connected to each other by the communication passage 163 in the base member 162.

While a column of microchips 106 (107, 108) (extending in vertical directions in FIG. 22) have been connected to each other by means of the communication passages 163 in this preferred embodiment, the present invention should not be limited thereto. For example, a row of microchips 106 through 108 of the first through third kinds (extending in lateral directions in FIG. 22) may be connected to each other by means of communication passages (not shown) formed in the base member 162. That is, the reservoirs 111A and 110A of adjacent two of microchips 106 of the first kind in lateral directions may be communicated with each other via a communication passage, the reservoir 111A of the microchip 106 of the first kind and the reservoir 114A of a microchip 107 of the second kind adjacent thereto in lateral directions being communicated with each other via a communication passage, and the reservoir 115A of the microchip 107 of the second kind and the reservoir 123A of a microchip 108 of the third kind adjacent thereto in lateral directions being communicated with each other via a communication passage, so that a sample may be continuously analyzed by means of the microchips 106 through 108.

Alternatively, sample receiving holes (not shown) may be recessed to be formed in portions of the base member 162 corresponding to the reservoirs 110A through 124A (see FIGS. 17A and 17B) of the microchips 106 through 108, the sample receiving hole of one of the microchips being connected to the sample receiving hole of the other microchip by means of a tube (passage) (not shown) embedded in the base member 162, so that a sample used in the one of the microchips may be continuously used in the other microchip.

Fourth Preferred Embodiment

Figure 23:
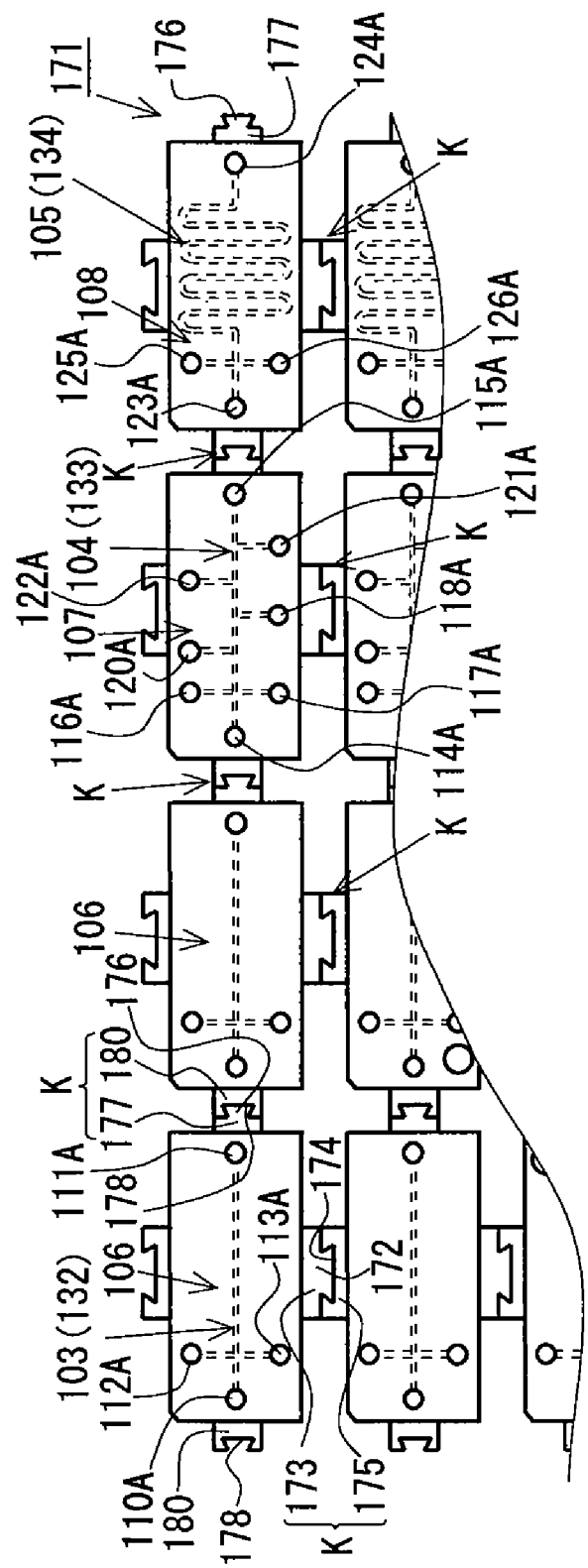
FIG. 23 is a plan view of a part of the fourth preferred embodiment of a microfluidic device according to the present invention.

FIG. 23 shows a microfluidic device 171 wherein a plurality of microchips 106 through 108 are connected to each other by connecting means K so as to be set in array. In this preferred embodiment, each of the microchips 106 through 108 has a first arm 173, which is formed on one of a pair of facing longer side faces and which has a protrusion 172 at the tip thereof, and a second arm 175 which is formed on the other side face of the pair of facing longer side faces and which has a recess 174 in the tip end. Each of the microchips 106 through 108 also has a third arm 177, which is formed on one of a pair of facing shorter side faces and which has a protrusion 176 at the tip thereof, and a fourth arm 180 which is formed on the other side face of the pair of facing shorter side faces and which has a recess 178 in the tip end thereof. The microchips 106 through 108 adjacent to each other in vertical directions in FIG. 23 are connected to each other by the engagement of the protrusion 172 of the first arm 173 with the recess 174 of the second arm 175. The microchips 106 through 108 adjacent to each other in lateral directions in FIG. 23 are connected to each other by the engagement of the protrusion 176 of the third arm 177 with the recess 178 of the fourth arm 180. That is, the first arm 173, second arm 175, third arm 177 and fourth arm 180 are associated with each other for forming the connecting means K.

In this preferred embodiment, a base member (not shown) for closing through holes 110 through 126 and fine grooves 103 through 105 on the side of the reverse is secured to the reverse of each of the microchips 106 through 108 so as to correspond to each of the microchips 106 through 108, so that reservoirs 110A through 126A and communication passages 132 through 134 are formed. The base member (not shown) may be formed of the same hard material as that of the microchips 106 through 108, or of a soft material, such as a film material.

With such a construction, an optional number of plural kinds of microchips 106 through 108 for different intended purposes or the like (e.g., the shape of microchannels and wells) can be freely combined.

Fifth Preferred Embodiment

Figure 24:
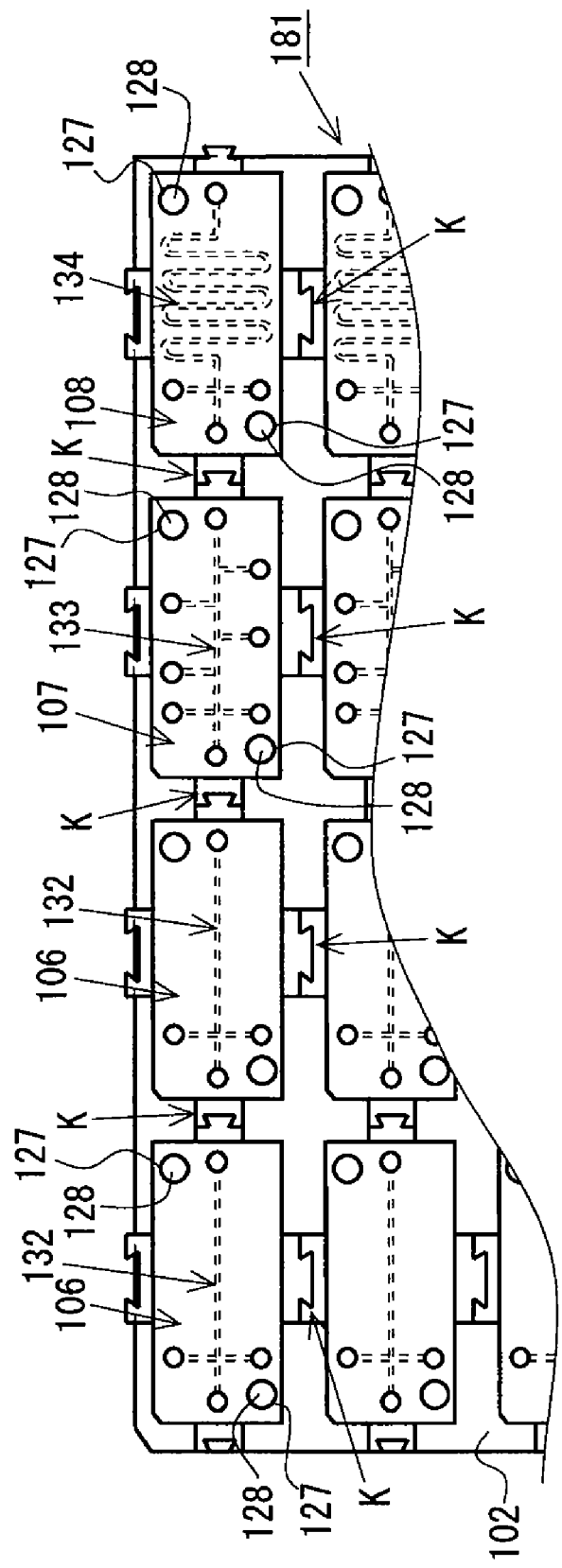
FIG. 24 is a plan view of a part of the fifth preferred embodiment of a microfluidic device according to the present invention.

FIG. 24 shows a microfluidic device 181 as a modified example of the fourth preferred embodiment shown in FIG. 23. In this preferred embodiment, a pair of positioning holes 127 are formed in the corner portions in directions of a diagonal line of each of the microchips 106 through 108, and a pair of positioning protrusions 128 engageable with the positioning holes 127 of a corresponding one of the microchips 106 through 108 are formed in a base member 102. Furthermore, in this preferred embodiment, holes (not shown) for receiving the positioning protrusions 28 are formed in the same base member as that in the fourth preferred embodiment. In this preferred embodiment, even if the microchips 106 through 108 are only supported on the base member 102, a sample in each of passages 132 through 134 of the microchips 106 through 108 does not leak out.

According to this preferred embodiment with such a construction, when the carriage or the like of the microfluidic device 181 having the microchips 106 through 108, which are connected to each other by the connecting means K to be set in array, is carried out, the connecting state of the microchips 106 through 108 is maintained by the base member 102, so that the carriage or the like of the microfluidic device 181 can be easily carried out. In addition, when a specific portion of the base member 102 is used as a reference point for continuously carrying out analysis, the position of analysis in each of the microchips 106 through 108 can be precisely determined, so that it is possible to decrease the dispersion in the results of analysis, which is caused by the dispersion in position of analysis.

Furthermore, when the base member 102 is caused to function as only a carrying tray, it is not required to position the microchips 106 through 108 on the base member 102. Therefore, it is not required to form the positioning holes 127 in the microchips 106 through 108, and it is not required to form the positioning protrusions 128 on the base member 102.

Sixth Preferred Embodiment

Figure 25:
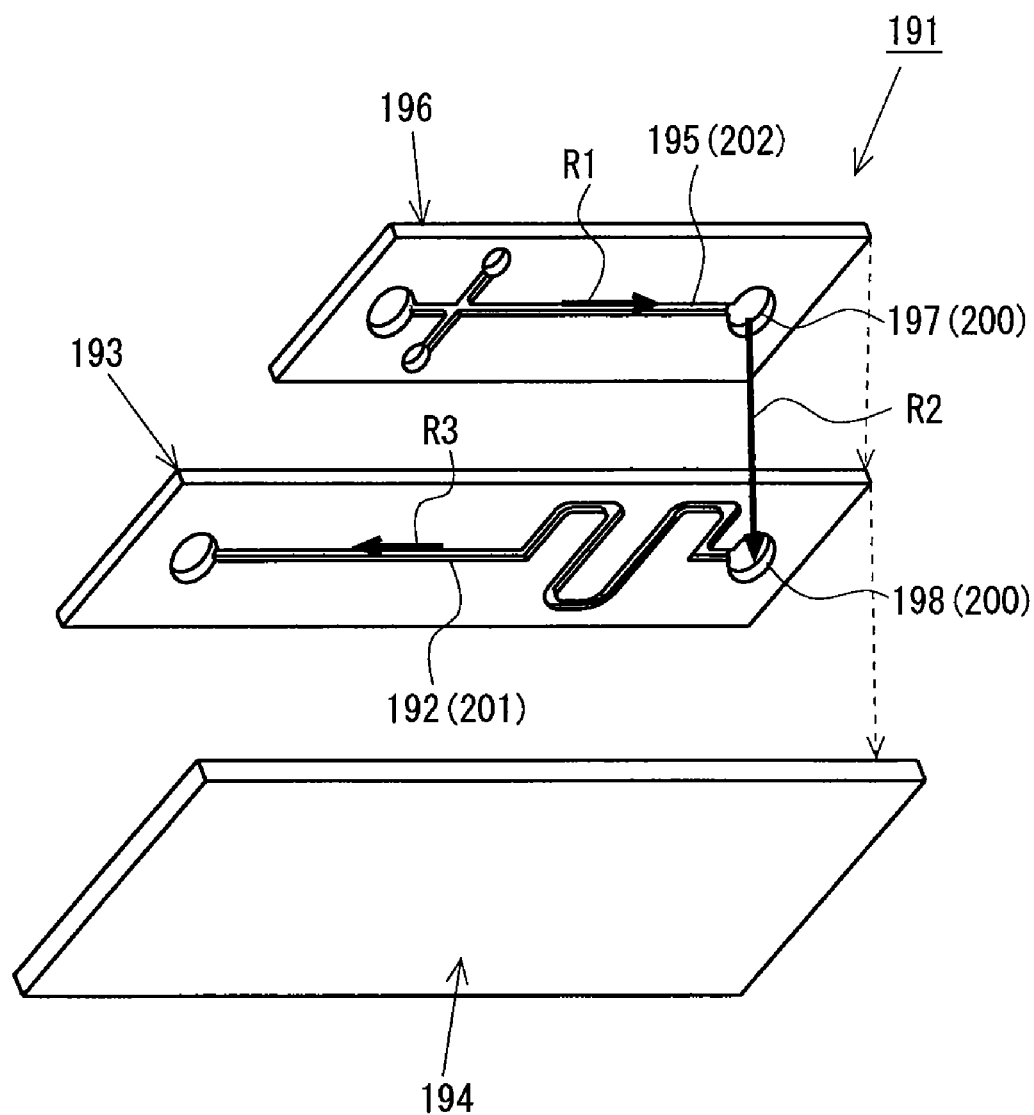
FIG. 25 is an exploded perspective view of the sixth preferred embodiment of a microfluidic device according to the present invention.

FIG. 25 is an exploded perspective view of the sixth preferred embodiment of a microfluidic device 191 according to the present invention. As shown in FIG. 25, a first microchip 193 having a fine groove (recessed portion) 192 is stacked on a base member 194 so that the surface of the first microchip 193 having the fine groove 192 faces the base member 194. In addition, a second microchip 196 having a fine groove (recessed portion) 195 is staked on the first microchip 193 so that the surface of the second microchip 196 having the fine groove 195 faces the first microchip 193 and so that a through hole 197 of the second microchip 196 is communicated with a through hole 198 of the first microchip 193. Thus, the base member 193, and first and second microchips 193 and 196 are associated with each other for forming the microfluidic device 191. Furthermore, the bonded surfaces of the first and second microchips 193 and 196 are connected or welded to each other to close the bottom end portion of the through hole 198 by the base member 194 to form a reservoir 200 and to close the openings of the fine grooves 192 and 195 by the base member 194 to form passages 201 and 202.

With such a construction, after a sample moves in the passage 202 of the second microchip 196 due to capillarity in a direction of arrow R1 to move in the reservoir 200 of the second microchip 196 and first microchip 192 in a direction of arrow R2, the sample moves in the passage 201 of the first microchip 193 due to capillarity in a direction of arrow R3.

If the plurality of microchips 193 and 196 are thus combined three-dimensionally (stacked in vertical directions), many analyses can be efficiently carried out in a narrow area. If such a construction is combined with the first preferred embodiment, it is possible to simultaneously carry out a larger number of analyses of samples, and it is possible to provide an inexpensive microfluidic device 191.

While the two microchips 193 and 196 have been stacked in this preferred embodiment, the present invention should not be limited thereto, but a larger number of microchips may be stacked.

As described above, in the microfluidic device according to the present invention, after the base member and various microchips are separately formed, microchips of kinds necessary for intended purpose, such as analysis of a sample, can be selected to be suitably combined to be positioned on the base member. Therefore, according to the present invention, when microchips are molded, a molding die can be miniaturized and easily worked, so that it is possible to decrease the cost of producing the die. Since the base member of a microfluidic device according to the present invention has a simple shape, it is possible to decrease the cost of producing the base member. As a result, the microfluidic device according to the present invention can be more inexpensively produced than a conventional device wherein a large number of microchannels are formed in a single plate so as to be set in array.

In the microfluidic device according to the present invention, various microchips having different structures of recessed portions can be suitably combined in accordance with intended purpose, such as analysis. Therefore, it is possible to easily carry out general purpose (e.g., mixing and analysis of a sample).

In the microfluidic device according to the present invention, the microchips are detachably held by the chip pressing claws formed on the base member. Therefore, even if the device drops onto the floor or the like to receive shocks, the microchips are not detached from the base member.

The microfluidic device according to the present invention can be utilized for various purposes by suitably combining various microchips. That is, the microfluidic device according to the present invention can be utilized as a chemical device for carrying out separation, analysis, mixing, reaction, concentration or the like of samples, e.g., fine organisms, such as viruses or bacterium, vital formations, such as cells or biopolymers, organic compounds other than biopolymers, inorganics, and inorganic compounds.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. A microfluidic device comprising:
   a base member;
   a plurality of microchips, each of which has a space defined therein for transporting a sample, said plurality of microchips being mounted on said base member so as to be set in array; and
   a chip pressing claw,
   wherein said plurality of microchips are detachably held by said chip pressing claw of said base member.

2. A microfluidic device as set forth in claim 1, wherein each of said plurality of microchips has a recessed portion which is closed by said base member to define said space.

3. A microfluidic device as set forth in claim 1, wherein said space is a passage for allowing said sample to move therein.

4. A microfluidic device as set forth in claim 3, wherein said passage has a storage portion for storing therein said sample.

5. A microfluidic device as set forth in claim 4, wherein said storage portion of one of said plurality of microchips is communicated with said storage portion of another of said plurality of microchips via a communication passage formed in said base member.

6. A microfluidic device as set forth in claim 1, wherein one of adjacent two of said plurality of microchips has an engaging protrusion which protrudes toward the other of the adjacent two of said plurality of microchips, and the other of the adjacent two of said plurality of microchips has an engaged recess which is engaged with said engaging protrusion of the one of adjacent two of said plurality of microchips.

7. A microfluidic device as set forth in claim 1, wherein said plurality of microchips are positioned with respect to said base member by positioning means.

* * * * *